(12) United States Patent
Iwahori et al.

(10) Patent No.: US 8,393,037 B2
(45) Date of Patent: Mar. 12, 2013

(54) ELECTRIC TOOTHBRUSH

(75) Inventors: Toshiyuki Iwahori, Kyoto (JP);
Akitoshi Miki, Ibaraki (JP); Kuniyoshi Takahashi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 7 days.

(21) Appl. No.: 12/922,597

(22) PCT Filed: Mar. 9, 2009

(86) PCT No.: PCT/JP2009/054423
§ 371 (c)(1),
(2), (4) Date: Sep. 14, 2010

(87) PCT Pub. No.: WO2009/113492
PCT Pub. Date: Sep. 17, 2009

(65) Prior Publication Data
US 2011/0010876 A1    Jan. 20, 2011

(30) Foreign Application Priority Data

Mar. 14, 2008  (JP) ................... 2008-065762
Nov. 13, 2008  (JP) ................... 2008-291285

(51) Int. Cl.
*A61C 17/34*    (2006.01)
(52) U.S. Cl. .................. 15/22.1; 340/573.1; 433/27
(58) Field of Classification Search .................. 15/22.1; 340/573.1; 433/27
See application file for complete search history.

(56) References Cited

U.S. PATENT DOCUMENTS 5,561,881 A * 10/1996 Klinger et al. ............. 15/22.1
2002/0133308 A1   9/2002 Lundell et al.

FOREIGN PATENT DOCUMENTS

| EP | 0 634 151 A3 | 1/1995 |
|---|---|---|
| JP | A-57-190506 | 11/1982 |
| JP | A-06-139937 | 5/1994 |
| JP | A-06-315413 | 11/1994 |
| JP | A-10-508765 | 9/1998 |
| JP | A-2000-116554 | 4/2000 |
| JP | A-2003-009950 | 1/2003 |
| JP | A-2003-501137 | 1/2003 |
| JP | A-2003-534095 | 11/2003 |
| JP | A-2005-152217 | 6/2005 |
| WO | WO 00/74591 A1 | 12/2000 |
| WO | WO 2006/137648 A1 | 12/2006 |

OTHER PUBLICATIONS

Russian Office Action in Russian Patent Application No. 2010141981; dated Jun. 7, 2011 (with English-language translation).
International Search Report in International Application No. PCT/JP2009/054423; dated Apr. 14, 2009 (with English-langauge translation).

*Primary Examiner* — Monica Carter
*Assistant Examiner* — Michael Jennings
(74) *Attorney, Agent, or Firm* — Oliff & Berridge, PLC

(57) ABSTRACT

A three-axis acceleration sensor is mounted to a body of an electric toothbrush. A CPU detects the three-dimensional attitude of the body based on an output from the acceleration sensor and, based on the attitude of the toothbrush, estimates which portion is being brushed. Then, the CPU measures by using a timer a brushing time of the portion being brushed. Results of brushing for each portion are evaluated and outputted based on the measured brushing time.

24 Claims, 35 Drawing Sheets

Fig. 11

| Part | Brushing time (sec) | Brush angle (°) | Brush pressure (g) | Brushing barometer |
|---|---|---|---|---|
| Maxillary anterior buccal side | 7.5 | 70 | 120 | 78 |
| Maxillary anterior lingual side | — | — | — | — |
| Maxillary left buccal side | 12.2 | 45 | 108 | 100 |
| Maxillary left lingual side | — | — | — | — |
| Maxillary right buccal side | — | — | — | — |
| Maxillary right lingual side | — | — | — | — |
| Mandibular anterior buccal side | — | — | — | — |
| Mandibular anterior lingual side | — | — | — | — |
| Mandibular left buccal side | 2.0 | 53 | 95 | 25 |
| Mandibular left lingual side | — | — | — | — |
| Mandibular right buccal side | — | — | — | — |
| Mandibular right lingual side | — | — | — | — |

Fig. 12
[15°]
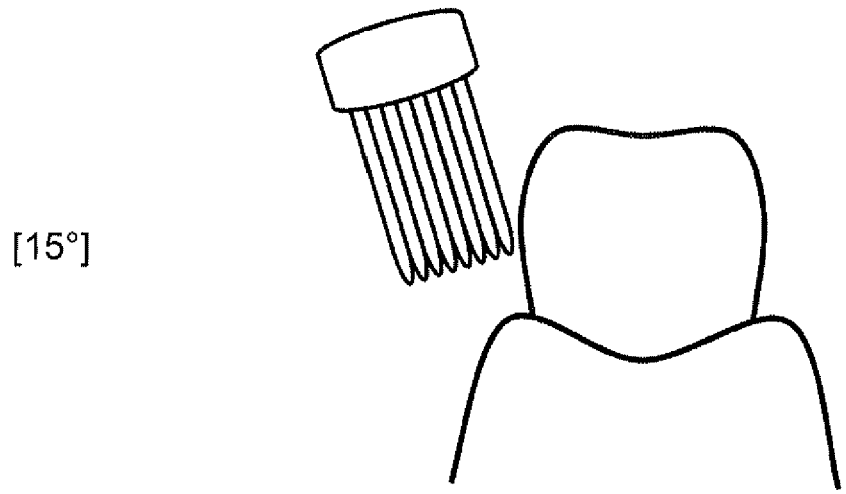
[45°]
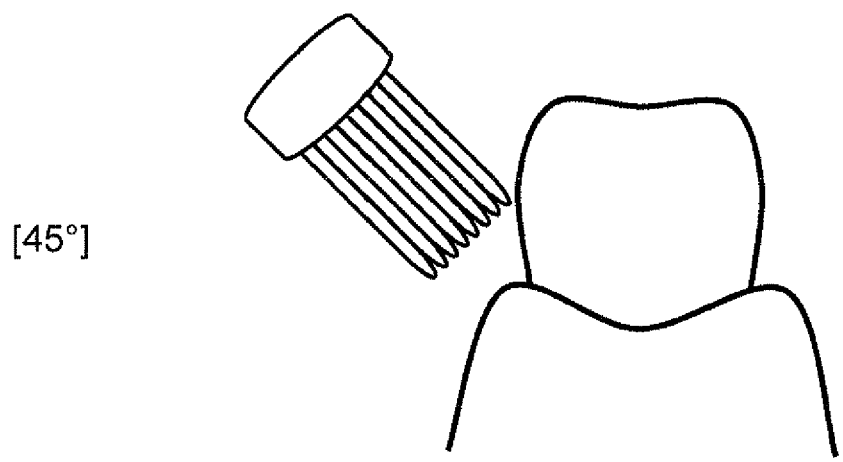
[90°]
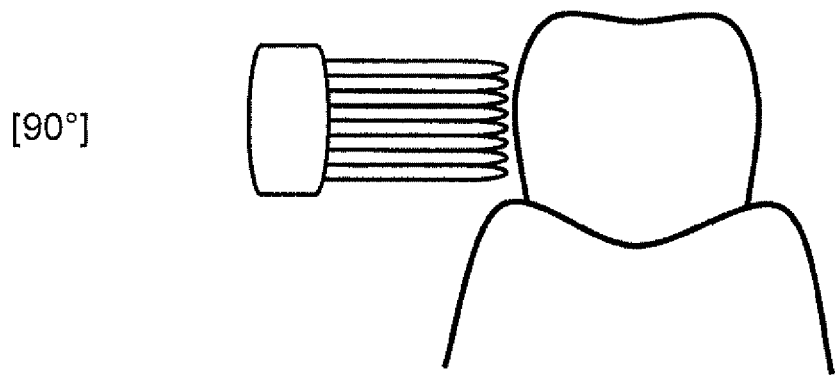

Fig. 32
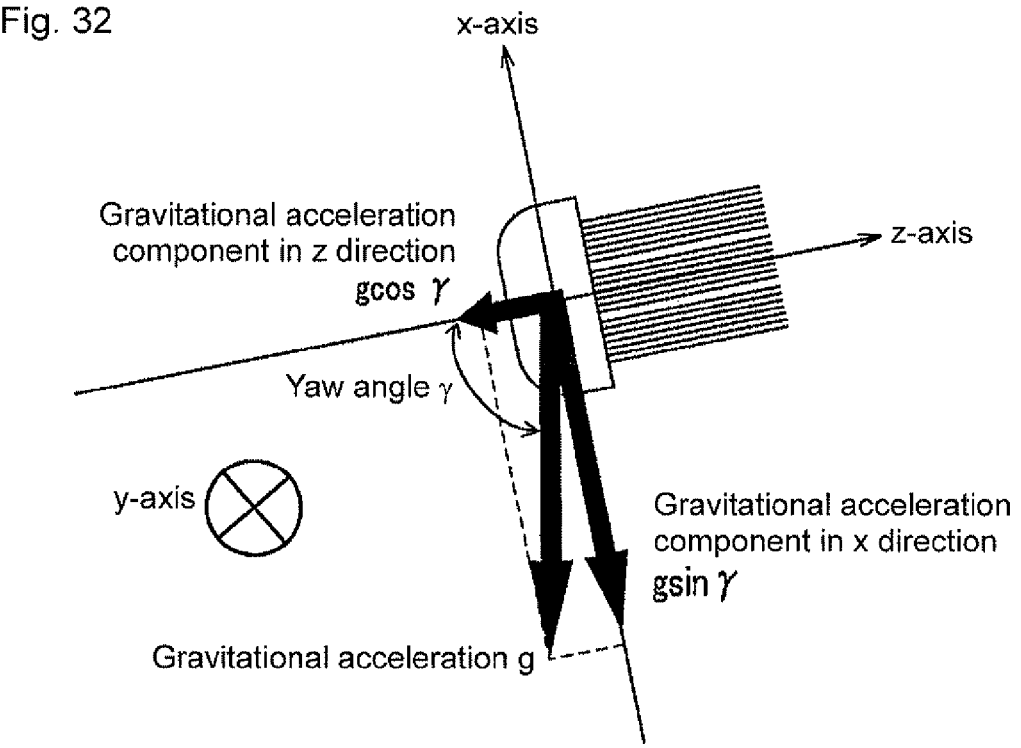
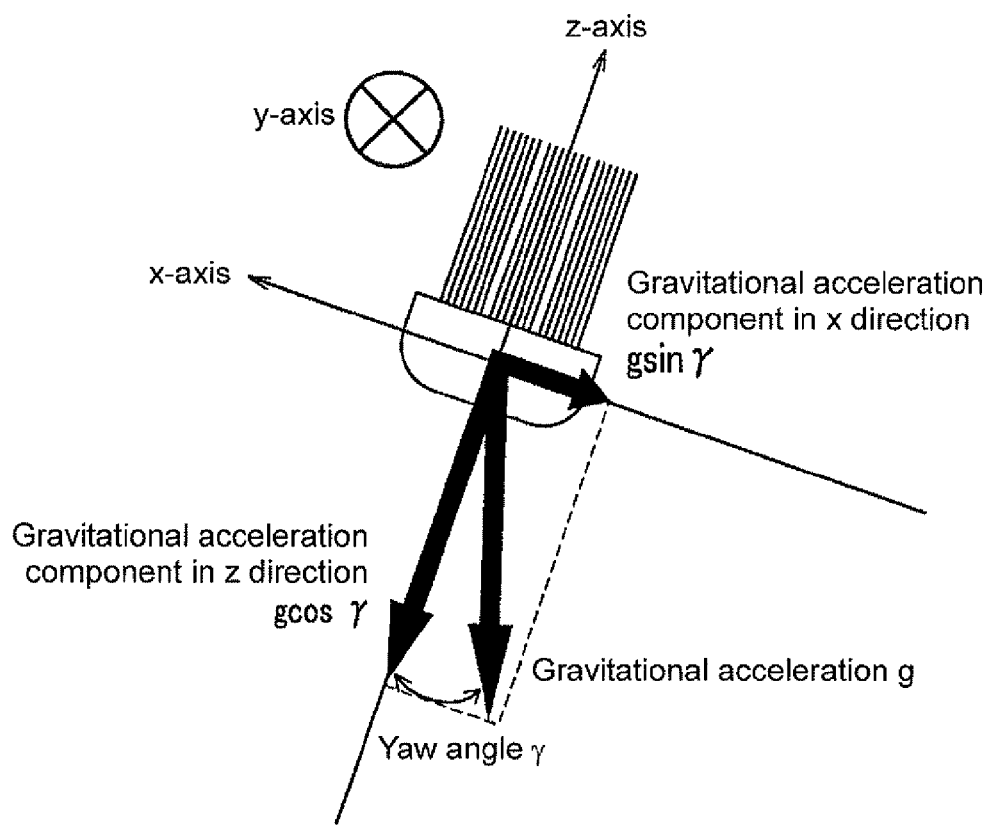

Fig. 34

|  | Optical sensor 41 | Optical sensor 42 | Optical sensor 43 | Optical sensor 44 |
|---|---|---|---|---|
| Maxillary left buccal side | ▲ | ▲ | × | ○ |
| Maxillary left occlusal surface | ▲ | ▲ | △ | △ |
| Maxillary left lingual side | ▲ | △ | ○ | △ |
| Maxillary anterior buccal side | ◎ | ◎ | ◎ | ○ |
| Maxillary anterior lingual side | ○ | ○ | ○ | ◎ |
| Maxillary right buccal side | ▲ | △ | × | ○ |
| Maxillary right occlusal surface | ▲ | ○ | △ | △ |
| Maxillary right lingual side | ▲ | ▲ | ○ | △ |
| Mandibular left buccal side | ▲ | △ | × | ○ |
| Mandibular left occlusal surface | ▲ | ○ | △ | △ |
| Mandibular left lingual side | ▲ | ▲ | ▲ | △ |
| Mandibular anterior buccal side | ◎ | ◎ | ◎ | ○ |
| Mandibular anterior lingual side | ○ | ○ | ○ | ◎ |
| Mandibular right buccal side | ▲ | ▲ | × | ○ |
| Mandibular right occlusal surface | ▲ | ▲ | △ | △ |
| Mandibular right lingual side | ▲ | △ | ▲ | △ |

◎ : Bright
○ : Relatively bright
△ : Slightly dark
▲ : Dark
× : Very dark

ELECTRIC TOOTHBRUSH

TECHNICAL FIELD

The present invention relates to an electric toothbrush.

BACKGROUND ART

Known ideas for assisting a correct way of using an electric toothbrush are as follows.

Patent Document 1 discloses a configuration in which brushing time, brush pressure and the left and right orientation of a brush are detected and achievement degrees of brushing respectively on the left and right sides are displayed. Patent Document 2 discloses a configuration in which when a toothbrush is taken out from a charger base, a timer is actuated so as to measure brushing time. Patent Document 3 discloses a configuration in which brushing time is accumulated only with appropriate brush pressure, and notification is performed when an accumulated value reaches preliminarily set target time. Patent Document 4 discloses an idea in which the orientation about an axis of a toothbrush main body is detected by four stages or eight stages, and a brushing part is estimated from the detection result. Specifically, a plurality of fan shape sections is provided in the circumferential direction inside the main body. By detecting in which section a conductive ball is in from a change in electric resistance, the orientation of the toothbrush main body is estimated. However, such a mechanism is not easily downsized. Since a position of the ball is not stabilized due to a motion of the toothbrush, it is difficult to obtain high detection precision. In Patent Document 4, the number and time of brushing are recorded for each part, and evaluation on whether or not the brushing is appropriately performed is outputted.

Patent Document 5 discloses an electric toothbrush in which intervals for brushing of areas in an oral cavity are continuously displayed. Patent Document 6 discloses a tool for learning tooth brushing for children in which the brushing order is guided by lighting each tooth in order in a display unit shaped like a tooth row.

Patent Document 1: Japanese Unexamined Patent Publication No. H6-315413
Patent Document 2: Japanese Unexamined Patent Publication (Translation of PCT Application) No. 2003-534095
Patent Document 3: Japanese Unexamined Patent Publication No. S57-190506
Patent Document 4: Japanese Unexamined Patent Publication No. 2005-152217
Patent Document 5: Japanese Unexamined Patent Publication (Translation of PCT Application) No. H10-508765
Patent Document 6: Japanese Unexamined Patent Publication No. 2000-116554

DISCLOSURE OF THE INVENTION

Problems to be Solved by the Invention

In a conventional electric toothbrush, it is difficult to precisely estimate a part being brushed. Thus, only an achievement degree in a roughly set division can be displayed, and usefulness and reliability are low as an evaluation guideline for brushing. With regard to a guide of brushing, a user is only guided as predetermined, indicating lack of flexibility.

In view of solving the above problems, it is an object of the present invention to provide a technique for assisting a proper way of using an electric toothbrush and a correct way of brushing.

Means for Solving the Problems

In order to achieve the above object, the following configurations are adopted in the present invention.

An electric toothbrush according to a first aspect of the present invention includes a brush, drive means for moving the brush, posture detection means for detecting a posture of the brush based on an output of an acceleration sensor, part estimation means for estimating a brushing part being brushed among a plurality of parts defined by dividing a surface of a tooth row based on the detected posture, time measurement means for measuring brushing time for each part, and evaluation output means for evaluating and outputting a brushing result for each part based on the measured brushing time.

By utilizing the output of the acceleration sensor, the posture of the brush can be highly precisely determined, and the brushing part can be identified with higher precision and more resolution capability than the conventional art. Therefore, the brushing result for a division (part) more finely divided than the conventional art can be evaluated, and a highly useful and reliable evaluation guideline can be provided to a user. Moreover, since the acceleration sensor is small in size, the acceleration sensor can be easily assembled into an electric toothbrush main body. A one-axis acceleration sensor can be used, and preferably multi-axis (two-axis, three-axis or more) acceleration sensor can also be used.

There is no need for providing all the configurations of the present invention in the electric toothbrush main body. Part of the configurations may be provided in an external device which is separated from the electric toothbrush main body (such as a charger for the toothbrush, a holder, and an exclusive indicator). In the latter case, the electric toothbrush of the present invention includes the electric toothbrush main body and the external device.

The electric toothbrush may further include brush angle estimation means for estimating a brush angle serving as an angle of the brush relative to a tooth axis based on the detected posture, and preferably, the evaluation output means further evaluates and outputs the brushing result for each part based on the estimated brush angle.

In a case where brushing is performed by an improper brush angle, a scale removing force is inferior to an optimum brush angle. Thus, there are possibilities that a desired brushing effect is not obtained and brushing takes time. With the configuration of the present invention, evaluation in consideration with the brush angle is outputted. Thus, the user can be aware of brushing by a correct brush angle.

The electric toothbrush may further include brush pressure detection means for detecting brush pressure, and preferably the evaluation output means further evaluates and outputs the brushing result for each part based on the detected brush pressure.

In a case where brushing is performed by the improper brush pressure, there is a possibility to cause a problem that the scale removing force is lowered, the brush life is reduced, or a burden on the gum is increased. The brush pressure of the electric toothbrush may be smaller than a normal toothbrush. Thus, it is said that most people who have just started using the electric toothbrush tend to apply excessive brush pressure. With the configuration of the present invention, the evaluation in consideration with the brush pressure is outputted. Thus, the user can be aware of brushing by correct brush pressure.

Items including the brushing time, the brush angle and the brush pressure may be separately evaluated or a plurality of the items may be comprehensively evaluated.

The electric toothbrush preferably further include brush angle guide means for comparing the estimated brush angle and a predetermined optimum value of the brush angle and outputting a guide for informing a user of whether or not the brush angle is proper.

Thereby, the user can understand the optimum brush angle and learn a correct way of brushing.

For example, the brush angle guide means preferably notifies that the brush angle is the optimum value or that the brush angle is not the optimum value.

Thereby, the user can easily recognize a correspondence (or a difference) between the brush angle and the optimum value. A method of the notification may be anything such as sound, light, vibration and voice.

Further, the brush angle guide means preferably stepwise changes a notification level in accordance with a degree of a difference between the brush angle and the optimum value.

The user can grasp that the brush angle comes close to the optimum value by the change in the notification level, and hence the brush angle can easily correspond to the optimum value.

The electric toothbrush preferably further includes brushing part guide means for determining and guiding a part to be brushed next among parts not sufficiently brushed yet based on the brushing result for each part.

With such a guide, brushing can be efficiently performed without leaving an unbrushed part. That is, the part to be brushed next is selected from the parts not sufficiently brushed yet. Thus, the unbrushed part is not left and useless actions such as brushing the same part repeatedly are eliminated. In the present invention, the part being actually brushed is identified. Thus, even in a case where the user brushes another part against the guide, the brushing result can be correctly recorded and evaluated, and the guide for the brushing order can be appropriately corrected.

The brushing part guide means preferably guides a change in the brushing part when a current brushing part is different from the part to be brushed.

In a case where the user is to brush an already-brushed part repeatedly or the like, the change in the brushing part is encouraged. Thus, brushing can be efficiently performed.

An electric toothbrush according to a second aspect of the present invention includes a brush, drive means for moving the brush, posture detection means for detecting a posture of the brush, part estimation means for estimating a brushing part being brushed among a plurality of parts defined by dividing a surface of a tooth row based on the detected posture, brush angle estimation means for estimating a brush angle serving as an angle of the brush relative to a tooth axis based on the detected posture, and brush angle guide means for comparing the estimated brush angle and an optimum value of the brush angle in the brushing part and outputting a guide for informing a user of whether or not the brush angle is proper. The brush angle guide means preferably notifies that the brush angle is the optimum value or that the brush angle is not the optimum value. The brush angle guide means preferably stepwise changes a notification level in accordance with a degree of a difference between the brush angle and the optimum value.

The above means and processes can be combined as far as possible so as to form the present invention.

EFFECT OF THE INVENTION

The present invention is capable of assisting a proper way of using an electric toothbrush and a correct way of brushing.

BRIEF DESCRIPTION OF THE DRAWINGS

FIG. 11 is a view showing one example of brushing information.

FIG. 12 is a view for illustrating a brush angle.

FIG. 32 is a view for illustrating posture detection of a ninth embodiment.

FIG. 34 is a table showing a relationship between the brushing part and outputs of optical sensors.

BEST MODE FOR CARRYING OUT THE INVENTION

Preferred embodiments of this invention will be described in detail as examples with reference to the drawings.
(First Embodiment)
(Configuration of Electric Toothbrush)

Figure 1:
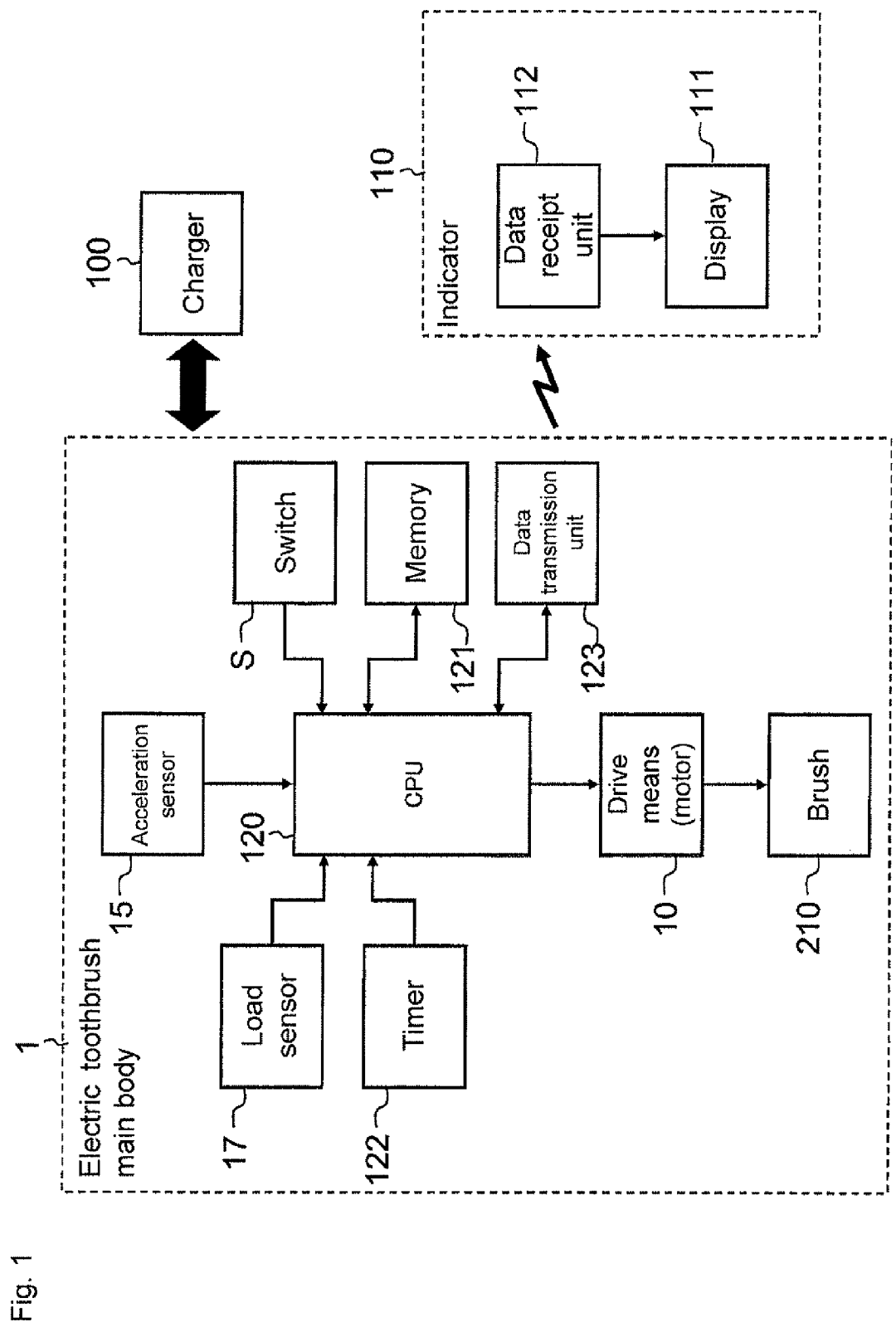
FIG. 1 is a block diagram of an electric toothbrush of a first embodiment.
Figure 2:
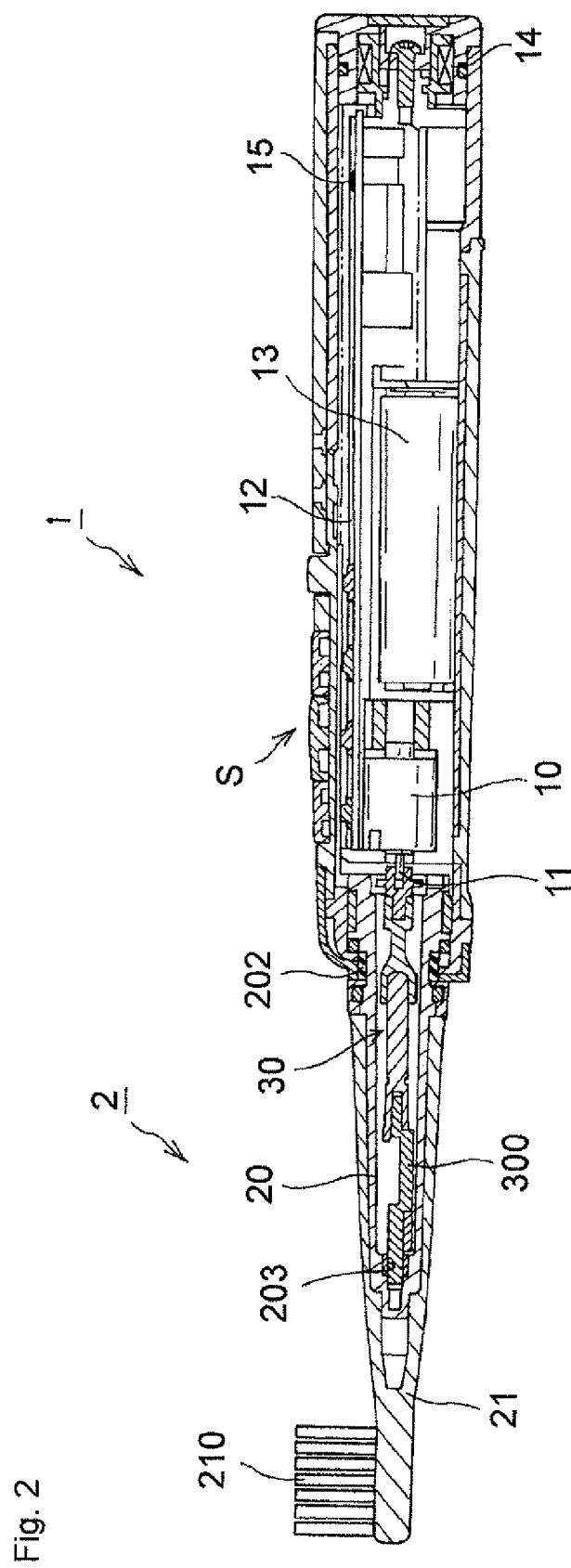
FIG. 2 is a sectional view showing an internal configuration of the electric toothbrush of the first embodiment.
Figure 3:
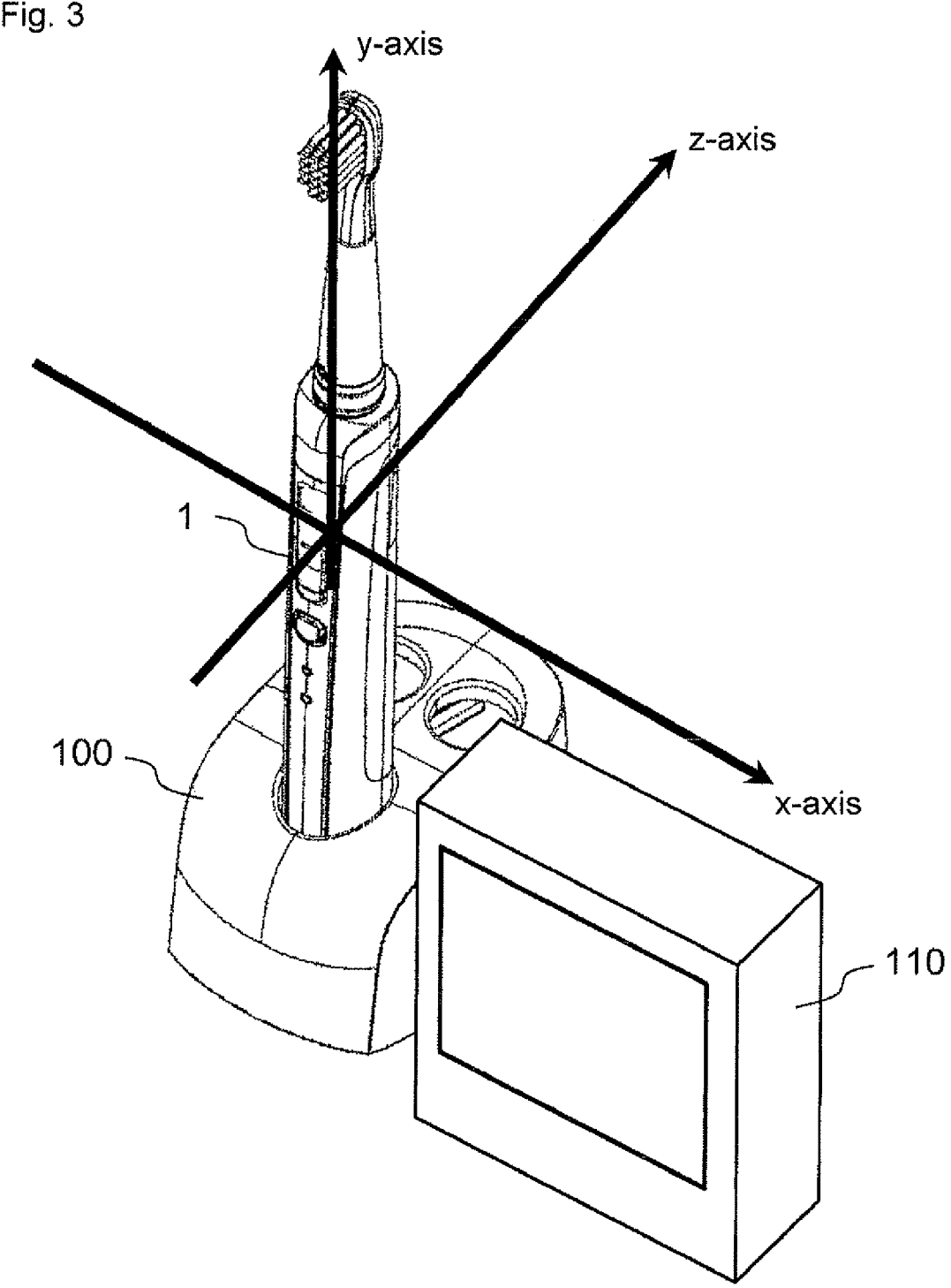
FIG. 3 is a perspective view showing an outer appearance of the electric toothbrush.

With reference to FIGS. 1, 2 and 3, a configuration of an electric toothbrush will be described. FIG. 1 is a block diagram of an electric toothbrush of a first embodiment, FIG. 2 is a sectional view showing an internal configuration of the electric toothbrush of the first embodiment, and FIG. 3 is a perspective view showing an outer appearance of the electric toothbrush.

The electric toothbrush is provided with an electric toothbrush main body 1 (hereinafter, also simply referred to as the "main body 1") in which a motor 10 serving as a drive source is built, a vibration member 2 having a brush 210. The main body 1 has a substantially cylindrical shape and also serves as a handle portion to be gripped by a user by hand at the time of brushing teeth. Further, the electric toothbrush of the present embodiment is provided with a charger 100 for resting and charging the main body 1, and an indicator 110 for outputting a brushing result.

A switch S for turning ON/OFF a power supply and switching an operation mode is provided in the main body 1. The motor 10 serving as the drive source, a drive circuit 12, a rechargeable battery 13 serving as 2.4 V power supply, a charging coil 14 and the like are provided inside the main body 1. At the time of charging the rechargeable battery 13, the main body 1 is simply rested on the charger 100 so that the rechargeable battery is contactlessly chargeable by electromagnetic induction. The drive circuit 12 has a CPU (an input and output processing unit) 120 for variously executing calculation and control, a memory 121 for storing a program and various set values, a timer 122, a data transmission unit 123 and the like. The data transmission unit 123 is communication means for wirelessly communicating with a data receipt unit 112 of the indicator 110. The indicator 110 is provided with a display 111 for outputting data received by the data receipt unit 112 such as the brushing result.

Further, a multi-axis (three-axis of x, y, z herein) acceleration sensor 15 is provided inside the main body 1. As shown in FIG. 3, the acceleration sensor 15 is installed with the x-axis parallel to a brush surface, the y-axis corresponding to the longitudinal direction of the main body 1, and the z-axis perpendicular to the brush surface. That is, a gravitational acceleration vector is parallel to the y-axis when the main body 1 is rested on the charger 100, parallel to the z-axis when the brush surface is turned toward the upper side, and parallel to the x-axis when the main body 1 is turned to be horizontal and the brush surface is turned toward the side. Outputs of the axes of the acceleration sensor 15 are inputted to the CPU 120 and utilized for detecting a three-dimensional posture of the brush.

Figure 29:
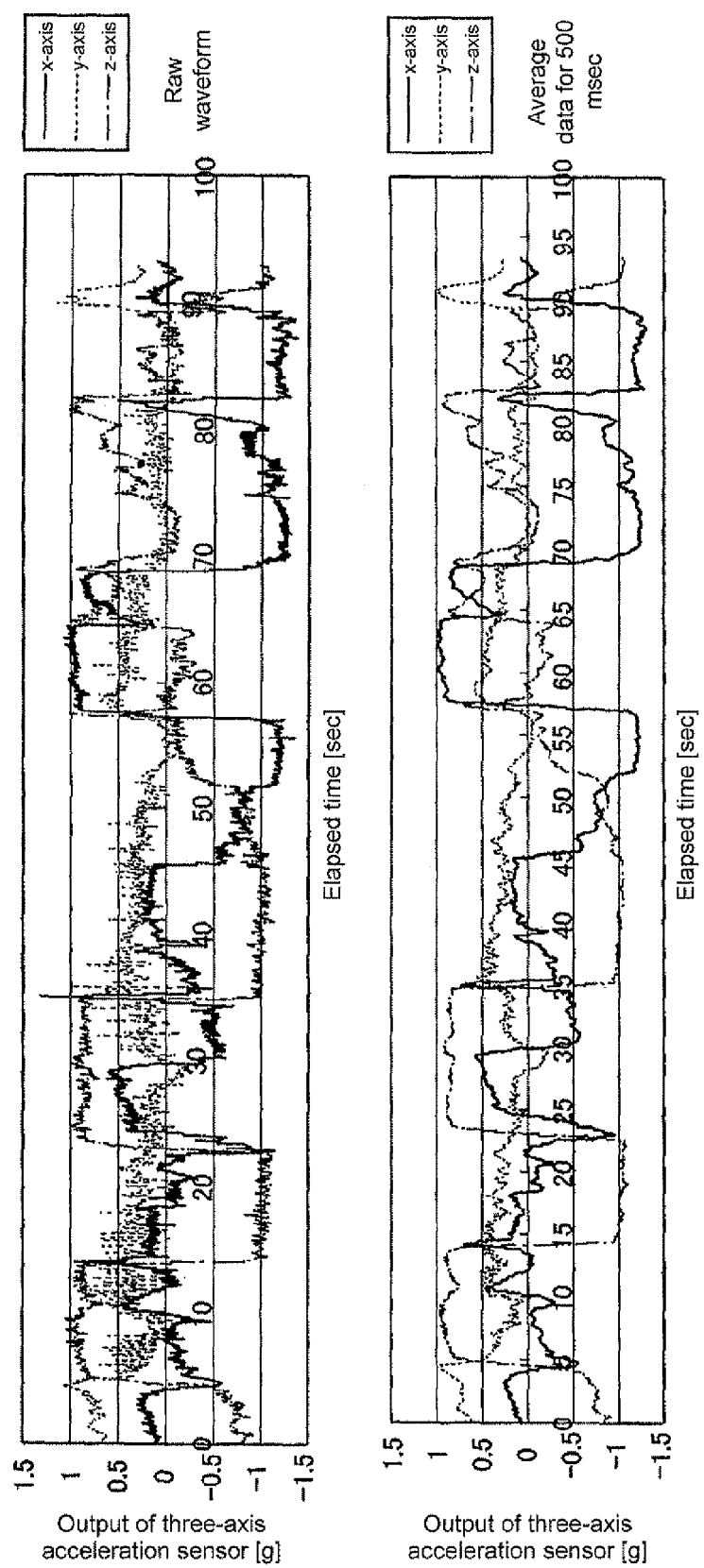
FIG. 29 is a graph for illustrating a decrease/increase in noise of the outputs of the acceleration sensor.

A piezoresistive type, capacitance type or thermal detection type MEMS sensor can be preferably utilized as the acceleration sensor 15. Since the MEMS sensor is very small in size, the sensor is easily assembled inside the main body 1. However, the type of the acceleration sensor 15 is not limited thereto, but an electrodynamic type, strain gauge type or piezoelectric type sensor may be utilized. Although not particularly shown in the drawings, a correction circuit for correcting balance between sensor sensitivities for the axes, temperature characteristics of the sensitivities, temperature drifts and the like may be provided. A band pass filter (low-pass filter) for eliminating a dynamic acceleration component and noise may be provided. The noise may be decreased by smoothing output waveforms of the acceleration sensor. FIG. 29 is an example that high-frequency noise of the output waveforms is decreased by averaging data for hundreds of msec.

A load sensor (brush pressure detection means) 17 for detecting brush pressure (a load imposed on the brush) is provided inside the main body 1. Any type of sensor including a strain gauge sensor, a load cell sensor and a pressure sensor can be utilized as the load sensor 17. However, a MEMS sensor can be favorably used by reason that the MEMS sensor is small in size so as to be easily assembled into the main body 1.

The vibration member 2 is provided with a stem portion 20 fixed to the side of the main body 1, and a brush component 21 installed to the stem portion 20. The brush 210 is implanted into a front end of the brush component 21. The brush component 21 is a consumable item and hence detachable from the stem portion 20 so as to be replaced by a new item.

The stem portion 20 is made of a resin material. The stem portion 20 is attached to the main body 1 via an elastic member 202 made of elastomer. The stem portion 20 is a tubular member with a closed front end (an end on the side of the brush) and has a bearing 203 on a front end inside the tube. A distal end of an eccentric shaft 30 coupled to a rotation shaft 11 of the motor 10 is inserted into the bearing 203 of the stem portion 20. The eccentric shaft 30 has a weight 300 in the vicinity of the bearing 203, and a gravity center of the eccentric shaft 30 is shifted from a rotation center thereof. A tiny clearance is provided between the distal end of the eccentric shaft 30 and the bearing 203.

(Drive Principle of Electric Toothbrush)

The CPU 120 supplies a drive signal corresponding to the operation mode (such as a pulse-width modulation signal) to the motor 10 so as to rotate the rotation shaft 11 of the motor 10. The eccentric shaft 30 is rotated in accordance with rotation of the rotation shaft 11. However, since the gravity center of the eccentric shaft 30 is shifted, the eccentric shaft performs a motion as if swirling around the rotation center. Thus, the distal end of the eccentric shaft 30 is repeatedly collided with an inner wall of the bearing 203 so as to vibrate (move) the stem portion 20 and the brush component 21 installed to the stem portion at high speed. That is, the motor 10 plays a role of drive means for vibrating (moving) the brush, and the eccentric shaft 30 plays a role of a motion transmission mechanism (a motion conversion mechanism) for converting an output (rotation) of the motor 10 into vibration of the vibration member 2.

A user can hold the main body 1 by hand and apply the brush 210 vibrating at high speed to the teeth so as to perform brushing. The CPU 120 monitors continued operation time by using the timer 122, and automatically stops the vibration of the brush when predetermined time (such as two minutes) elapses.

In the electric toothbrush of the present embodiment, the eccentric shaft 30 serving as the motion transmission mechanism is accommodated in the vibration member 2, and particularly the weight 300 is arranged in the vicinity of the brush 210. Thus, a part of the brush 210 can be efficiently vibrated. Meanwhile, since the vibration member 2 (the stem portion 20) is attached to the main body 1 via the elastic member 202, the vibration of the vibration member 2 is not easily transmitted to the main body 1. Thus, the vibration of the main body 1 and the hand at the time of brushing the teeth can be reduced, and hence feel of use can be improved.

(Operation of Electric Toothbrush)

A food residue and plaque are differently attached in accordance with a type of tooth (such as tooth on the maxilla/mandible, and molar/incisor tooth) and a part (the lingual/buccal side, and a tooth/occlusal surface). Thus, an effective brushing operation varies according to a part of a tooth row, in terms of a way of applying the brush (a brush angle and the brush pressure), a way of moving, speed, brushing time and the like. Therefore, evaluation on whether or not brushing is properly performed is desirably performed for each part.

The electric toothbrush of the present embodiment is to realize brushing evaluation for each part by precisely estimating a brushing part based on a posture of the brush detected by the acceleration sensor 15. Although there are various evaluation items, three items of the brushing time, the brush angle and the brush pressure are evaluated here.

Figure 4:
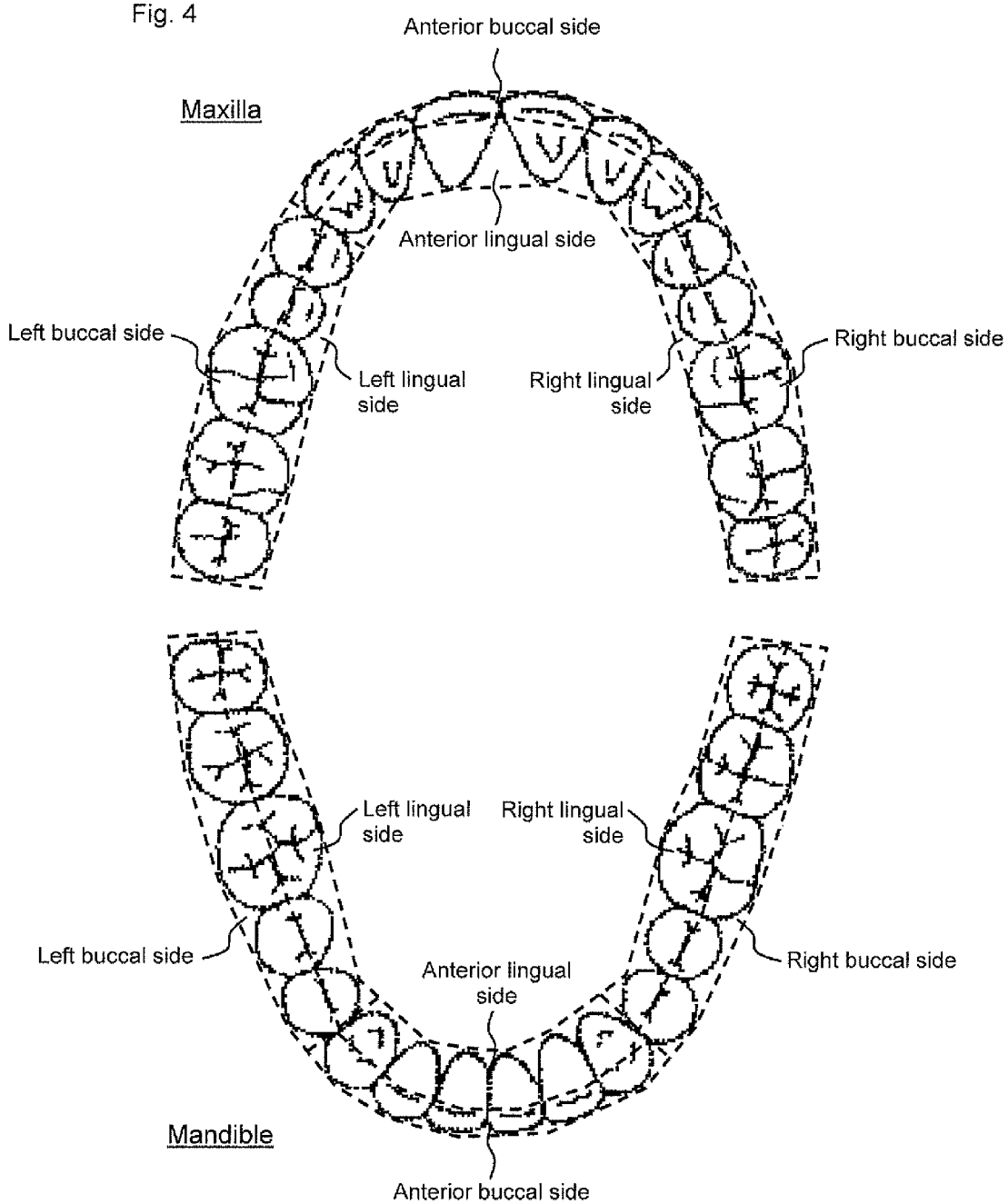
FIG. 4 is a view showing sections of a brushing part.

In the present embodiment, as shown in FIG. 4, upper and lower tooth rows are divided into 12 parts including the "maxillary anterior buccal side", the "maxillary anterior lingual side", the "maxillary left buccal side", the "maxillary left lingual side", the "maxillary right buccal side", the "maxillary right lingual side", the "mandibular anterior buccal side", the "mandibular anterior lingual side", the "mandibular left buccal side", the "mandibular left lingual side", the "mandibular right buccal side", and the "mandibular right lingual side". However, division of the tooth rows is not limited thereto but the tooth rows may be more roughly divided or more finely divided. For example, upper, lower, left and right occlusal surfaces may be taken into consideration.

Figure 5:
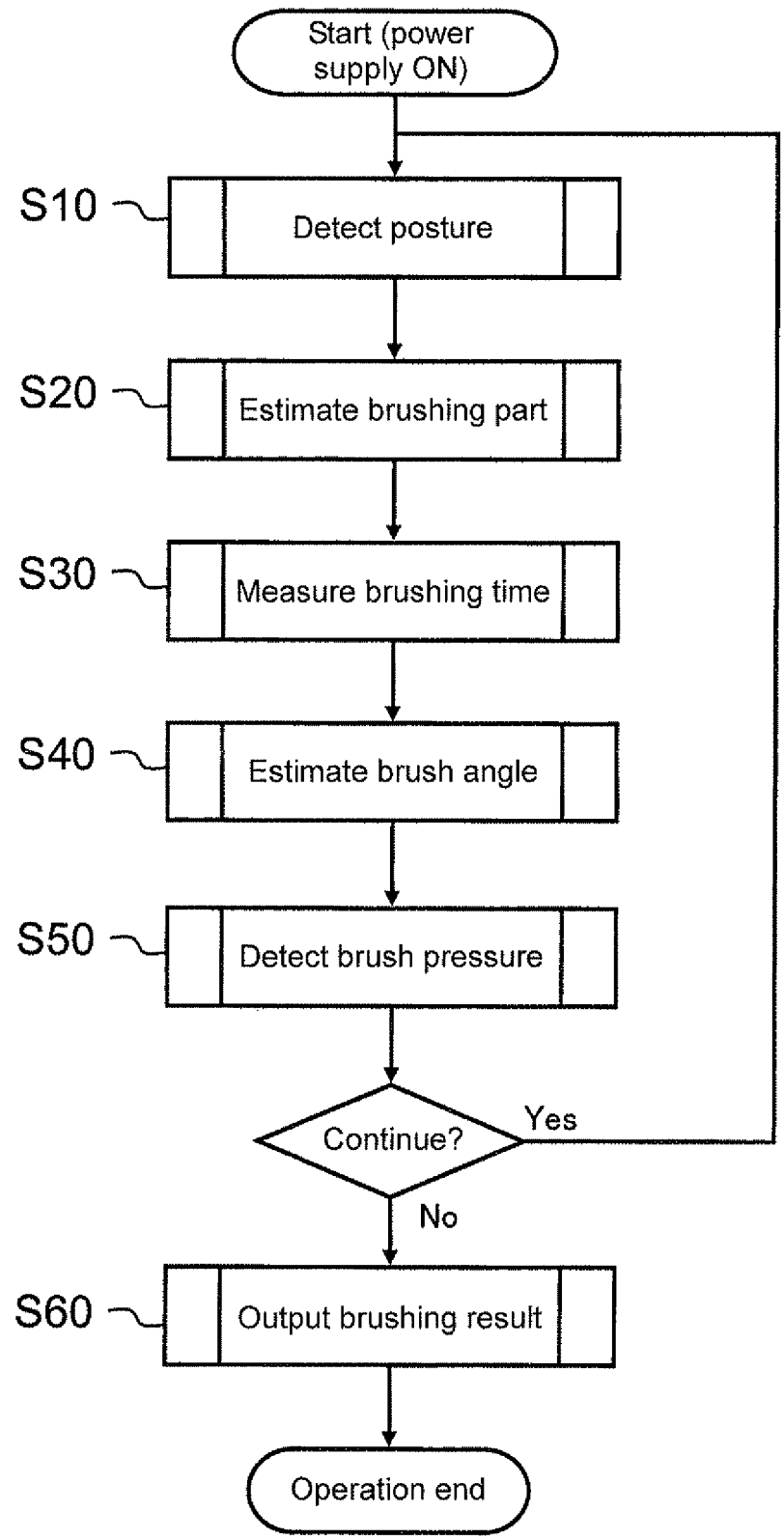
FIG. 5 is a flowchart showing a main routine of a brushing evaluation process of the first embodiment.
Figure 6:
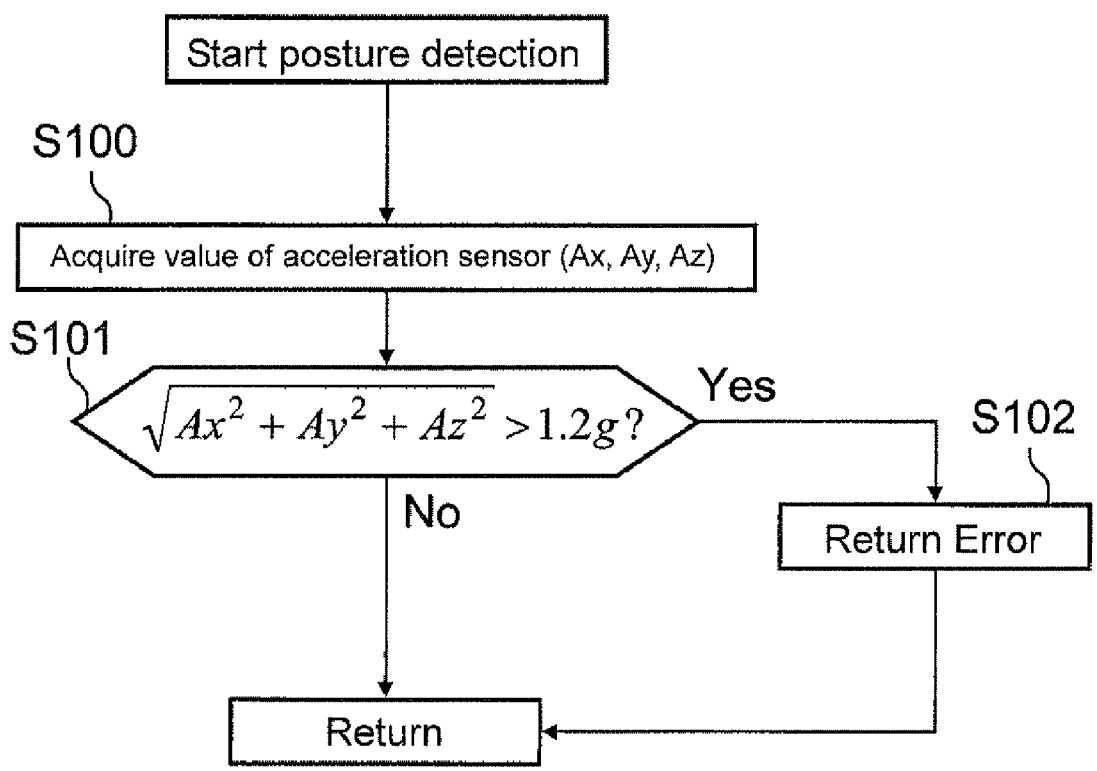
FIG. 6 is a flowchart of a posture detection process of the first embodiment.
Figure 7:
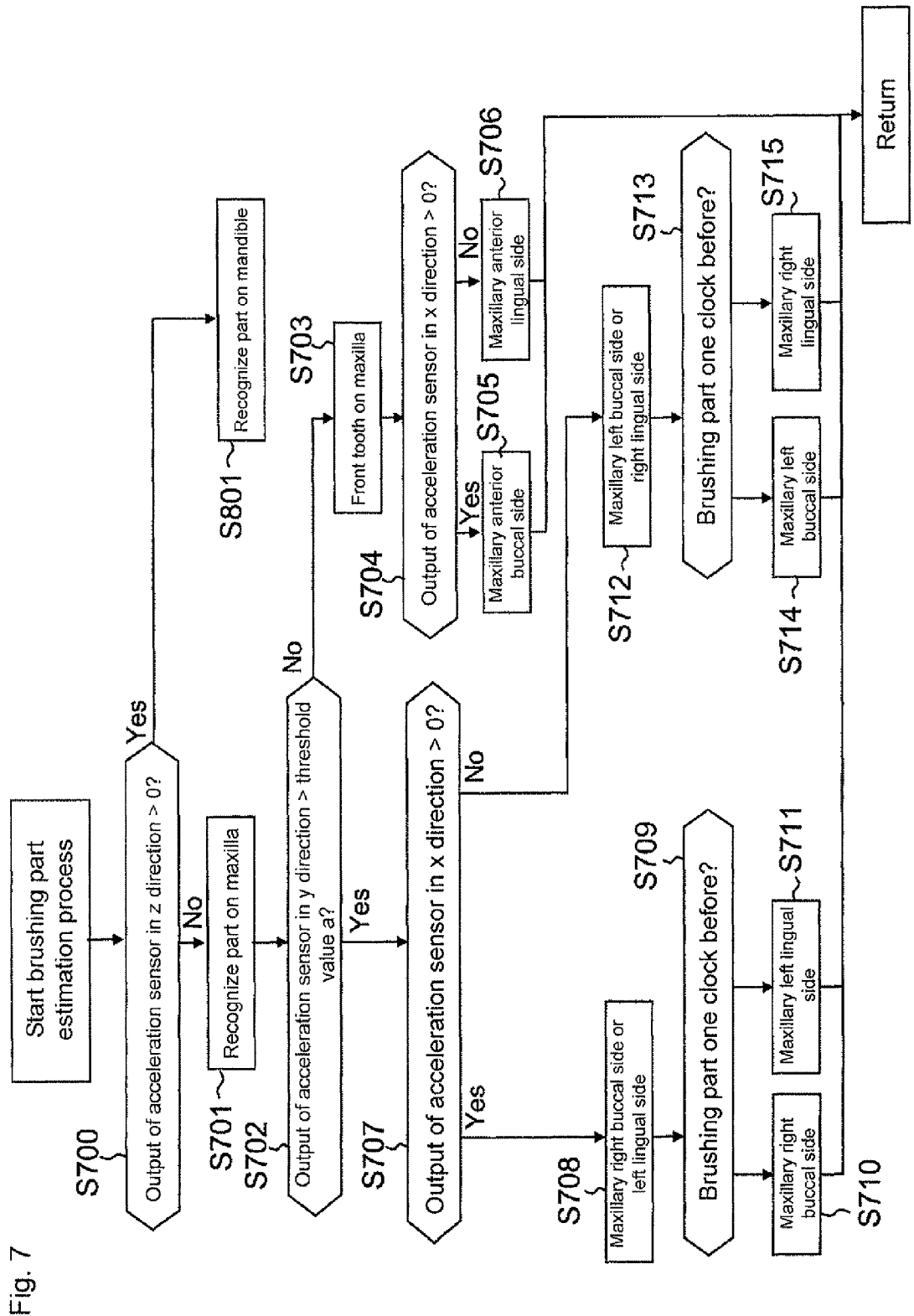
FIG. 7 is a flowchart of a brushing part estimation process (a maxilla) of the first embodiment.
Figure 8:
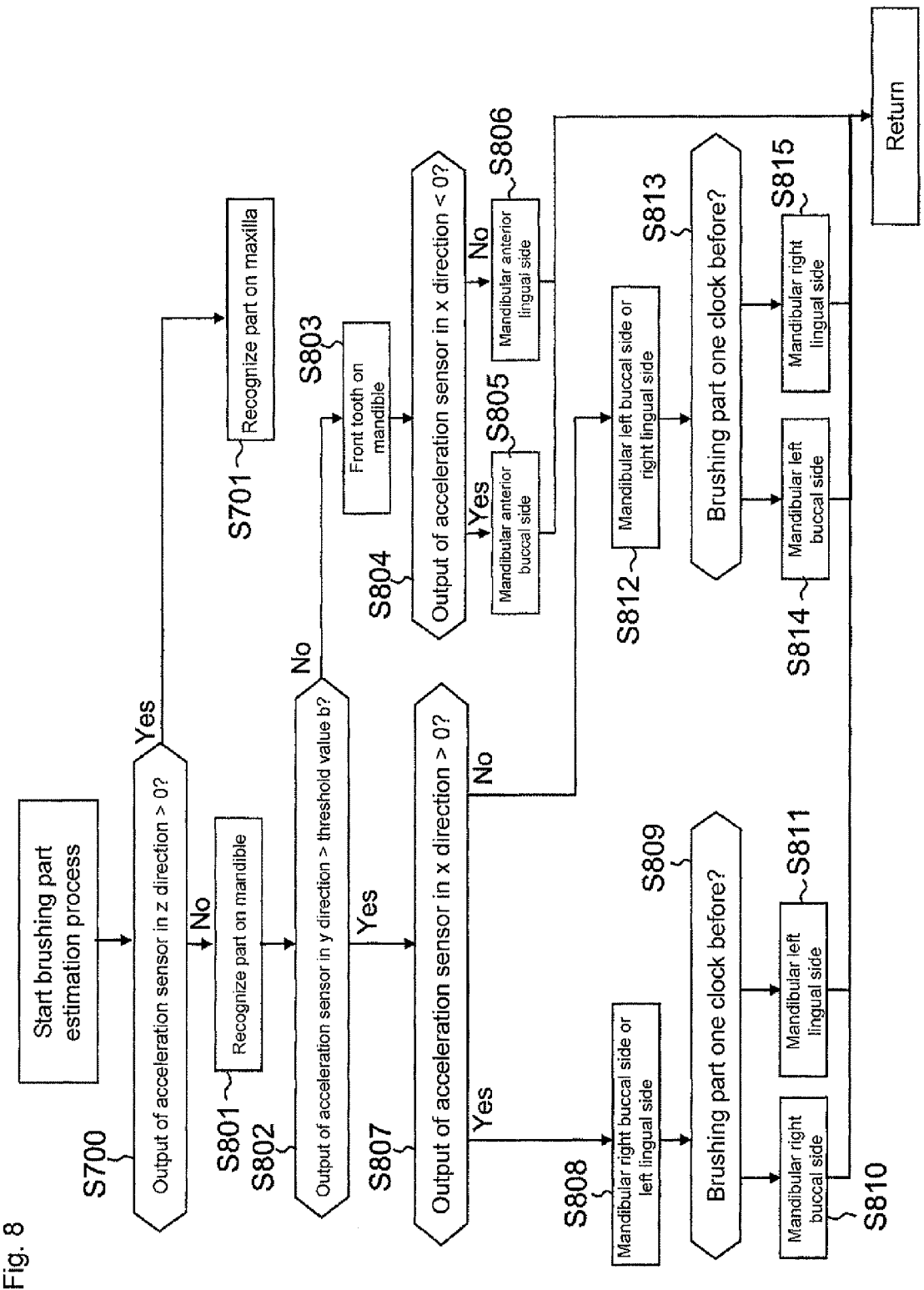
FIG. 8 is a flowchart of a brushing part estimation process (a mandible) of the first embodiment.

With reference to flowcharts of FIGS. 5 to 8, a flow of the brushing evaluation will be specifically described. FIG. 5 is a flowchart of a main routine, and FIGS. 6 to 8 are flowcharts showing details of processes of the main routine. The processes described below serve as processes to be executed by the CPU 120 in accordance with the program unless otherwise specified.

When the power supply of the electric toothbrush is turned ON, the CPU 120 detects the posture (inclination) of the brush based on the outputs of the acceleration sensor 15 (S10). Next, the CPU 120 estimates the brushing part based on the posture detected in S10 (S20). Next, the CPU 120 measures the brushing time (S30), estimates the brush angle (S40), and detects the brush pressure (S50). These information are recorded in the memory for each part (refer to FIG. 11). The processes S10 to S50 are repeatedly executed once every fixed time. When the power supply is turned OFF or the continued operation time reaches predetermined time (such as two minutes), the CPU 120 evaluates the brushing result for each part based on the brushing information (the brushing time, the brush angle and the brush pressure) recorded in the memory, and outputs evaluation results to the display unit 110 (S60). The brushing information in the memory are cleared every time when the power supply of the electric toothbrush is turned ON.

Hereinafter, the processes S10 to S60 will be described in detail.

(Detection of Posture)

FIG. 6 is a flowchart of a posture detection process (S10).

The CPU 120 acquires respective outputs Ax, Ay, Az of the x, y, z-axes from the acceleration sensor 15 (S100). The output Ax indicates an acceleration component in the x direction, the output Ay indicates an acceleration component in the y direction, and the output Az indicates an acceleration component in the z direction. When the toothbrush is in a static state (when dynamic acceleration does not act on the acceleration sensor 15), a synthetic vector A of Ax, Ay, Az corresponds to gravitational acceleration. Here, "A=(Ax, Ay, Az)" is called a posture vector.

In a case where the posture vector A=(Ax, Ay, Az) is larger than 1.2 g (g indicates the gravitational acceleration) (S101; YES), an error is returned (S102). This is because when the dynamic acceleration component is largely included in the outputs of the acceleration sensor, the direction of the gravitational acceleration (that is, the three-dimensional posture of the brush) is not easily accurately identified. Instead of returning the error as in S102, the processes S100 and S101 may be repeated until the outputs Ax, Ay, Az of the acceleration sensor with the synthetic vector of not less than 1.2 g are obtained. A threshold value of the error determination is not limited to 1.2 g but other values.

(Estimation of Brushing Part)

Figure 9:
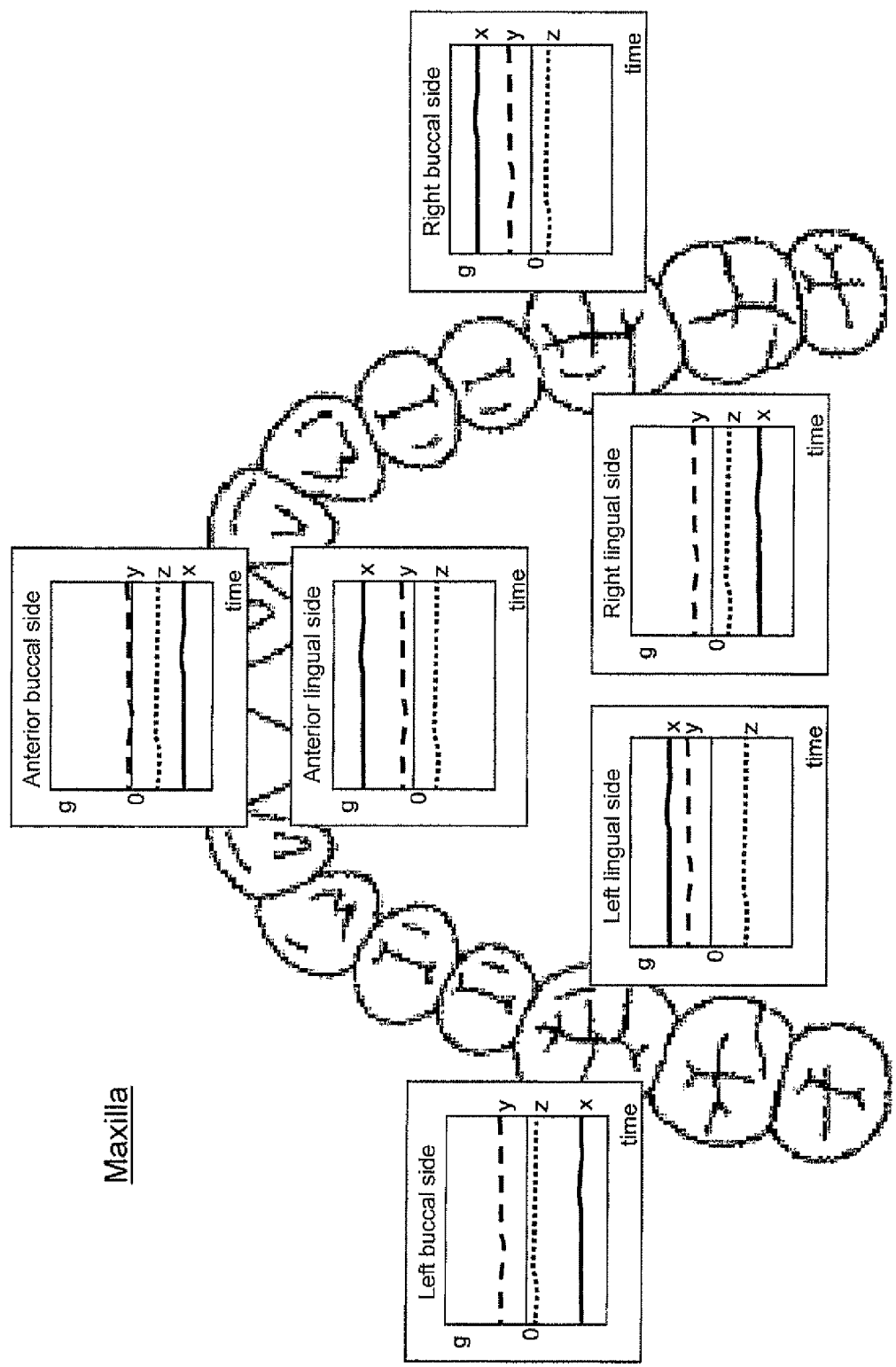
FIG. 9 is a view showing one example of outputs Ax, Ay, Az of an acceleration sensor for each brushing part on the maxilla.
Figure 10:
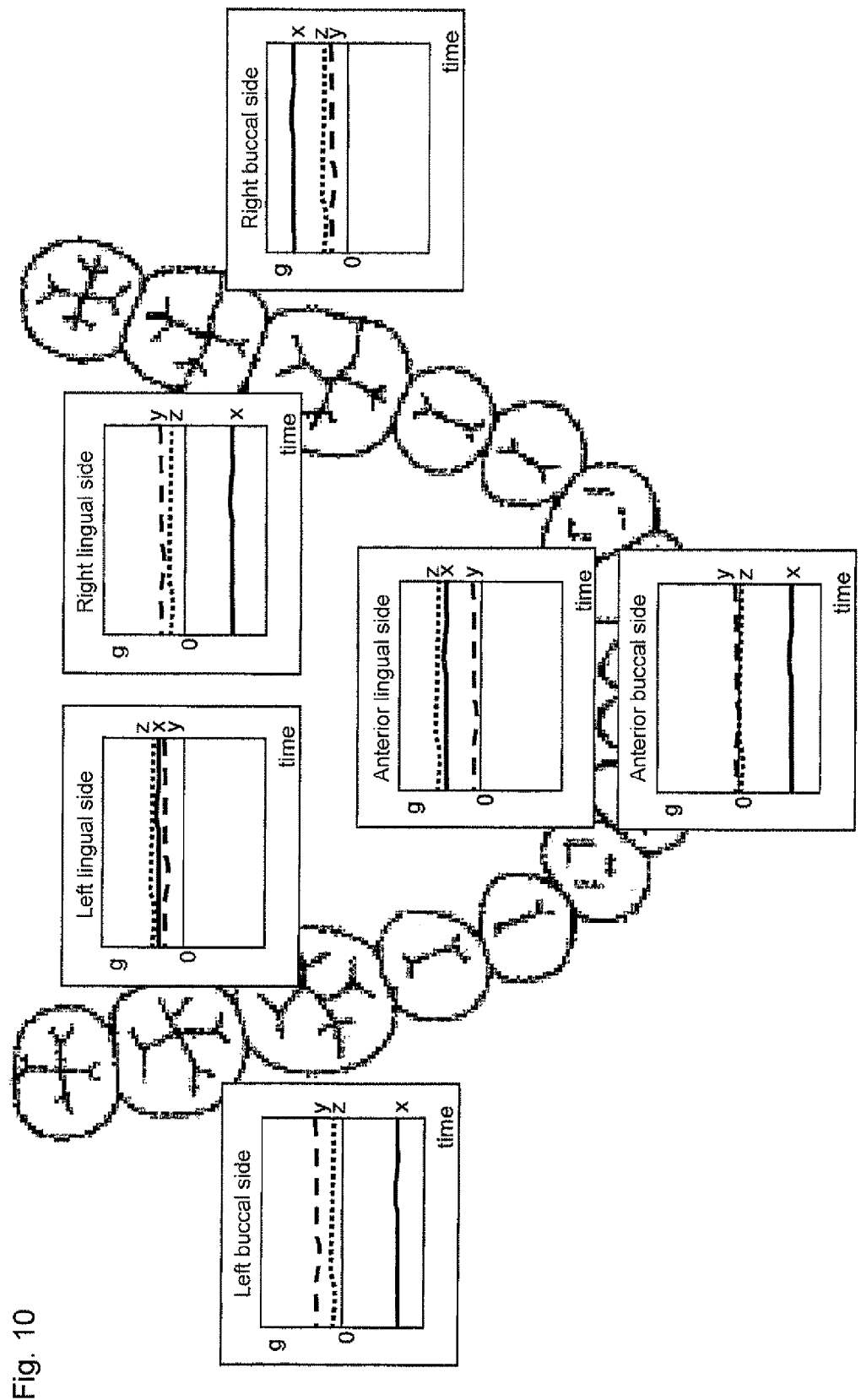
FIG. 10 is a view showing one example of outputs Ax, Ay, Az of the acceleration sensor for each brushing part on the mandible.

FIGS. 7 and 8 are flowcharts of brushing part estimation processes (S20). FIGS. 9 and 10 are views showing examples of the outputs Ax, Ay, Az of the acceleration sensor for each brushing part.

Firstly, the CPU 120 determines whether the part is on the maxilla or the mandible based on the output Az of the acceleration sensor in the z direction (S700). The determination is based on the fact that the brush surface is turned toward the upper side more than a little when the tooth row on the maxilla is brushed, and turned toward the lower side more than a little when the tooth row on the mandible is brushed. The part is determined to be on the mandible in a case of Az>0 (S801), and to be on the maxilla in a case of Az≦0 (S701).

(1) On Maxilla

The CPU 120 determines whether or not the part is a front tooth based on the output Ay of the acceleration sensor in the y direction (S702). The determination is based on the fact that the toothbrush main body 1 is relatively horizontal when the front tooth is brushed, but unavoidably oblique due to contact with lips when the molar tooth is brushed. The part is determined to be the front tooth on the maxilla in a case of Ay≦threshold value a (S703).

In a case where the part is determined to be the front tooth on the maxilla, the CPU 120 determines whether the part is on the buccal side or the lingual side based on the output Ax of the acceleration sensor in the x direction (S704). The determination is based on the fact that the orientation of the brush is turned over between the buccal side and the lingual side. The part is determined to be on the "maxillary anterior buccal side" in a case of Ax>0 (S705), and to be on the "maxillary anterior lingual side" in a case of Ax≦0 (S706).

Meanwhile, in a case where the part is determined to be a non-front tooth on the maxilla in S702, the CPU 120 determines the orientation of the brush based on the output Ax of the acceleration sensor in the x direction (S707). The part is determined to be on the "maxillary right buccal side or maxillary left lingual side" in a case of Ax>0 (S708), and to be on the "maxillary left buccal side or maxillary right lingual side" in a case of Ax≦0 (S712).

The maxillary right buccal side and the maxillary left lingual side, and the maxillary left buccal side and the maxillary right lingual side are not easily distinguished only by the outputs of the acceleration sensor. Thus, the CPU 120 narrows down a range to which the part belongs based on the brushing part determined in the previous process (the process one-clock before) (S709, S713). Specifically, in S709, when the previous brushing part is on any of the "maxillary anterior buccal side, maxillary right buccal side, maxillary right lingual side, mandibular anterior buccal side, mandibular right buccal side, and mandibular right lingual side", a current brushing part is estimated to be on the "maxillary right buccal side" (S710), and when the previous brushing part is on any of the "maxillary anterior lingual side, maxillary left buccal side, maxillary left lingual side, mandibular anterior lingual side, mandibular left buccal side, and mandibular left lingual side", the current brushing part is estimated to be on the "maxillary left lingual side" (S711). In S713, when the previous brushing part is on any of the "maxillary anterior buccal side, maxillary left buccal side, maxillary left lingual side, mandibular anterior buccal side, mandibular left buccal side, and mandibular left lingual side", the current brushing part is estimated to be on the "maxillary left buccal side" (S714), and when the previous brushing part is on any of the "maxillary anterior lingual side, maxillary right buccal side, maxillary right lingual side, mandibular anterior lingual side, mandibular right buccal side, and mandibular right lingual side", the current brushing part is estimated to be on the "maxillary right lingual side" (S715). Such estimation is performed based on high probability that the brushing part is moved so as to reduce a movement amount of the brush and changes in the orientation as far as possible.

(2) On Mandible

The CPU 120 determines whether or not the part is the front tooth based on the output Ay of the acceleration sensor in the y direction (S802). The determination is based on the fact that the toothbrush main body 1 is relatively horizontal when the front tooth is brushed, but unavoidably oblique due to contact with the lips when the molar tooth is brushed. The part is determined to be the front tooth on the mandible in a case of Ay≦threshold value b (S803).

In a case where the part is determined to be the front tooth on the mandible, the CPU 120 determines whether the part is on the buccal side or the lingual side based on the output Ax of the acceleration sensor in the x direction (S804). The determination is based on the fact that the orientation of the brush is turned over between the buccal side and the lingual side. The part is determined to be on the "mandibular anterior buccal side" in a case of Ax<0 (S805), and to be on the "mandibular anterior lingual side" in a case of Ax≧0 (S806).

Meanwhile, in a case where the part is determined to be the non-front tooth on the mandible in S802, the CPU 120 determines the orientation of the brush based on the output Ax of the acceleration sensor in the x direction (S807). The part is determined to be on the "mandibular right buccal side or mandibular left lingual side" in a case of Ax>0 (S808), and to be on the "mandibular left buccal side or mandibular right lingual side" in a case of Ax≦0 (S812).

In S809, when the previous brushing part is on any of the "mandibular anterior buccal side, mandibular right buccal side, mandibular right lingual side, mandibular anterior buccal side, maxillary right buccal side, and maxillary right lingual side", the current brushing part is estimated to be on the "mandibular right buccal side" (S810), and when the previous brushing part is on any of the "mandibular anterior lingual side, mandibular left buccal side, mandibular left lingual side, maxillary anterior lingual side, maxillary left buccal side, and maxillary left lingual side", the current brushing part is estimated to be on the "mandibular left lingual side" (S811). In S813, when the previous brushing part is on any of the "mandibular anterior buccal side, mandibular left buccal side, mandibular left lingual side, maxillary anterior buccal side, maxillary left buccal side, and maxillary left lingual side", the current brushing part is estimated to be on the "mandibular left buccal side" (S814), and when the previous brushing part is on any of the "mandibular anterior lingual side, mandibular right buccal side, mandibular right lingual side, maxillary anterior lingual side, maxillary right buccal side, and maxillary right lingual side", the current brushing part is estimated to be on the "mandibular right lingual side" (S815).

With the above processes, the current brushing part is identified to be on any of the "maxillary anterior buccal side" (S705), the "maxillary anterior lingual side" (S706), the "maxillary right buccal side" (S710), the "maxillary left lingual side" (S711), the "maxillary left buccal side" (S714), the "maxillary right lingual side" (S715), the "mandibular anterior buccal side" (S805), the "mandibular anterior lingual side" (S806), the "mandibular right buccal side" (S810), the "mandibular left lingual side" (S811), the "mandibular left buccal side" (S814), and the "mandibular right lingual side" (S815).

Figure 30:
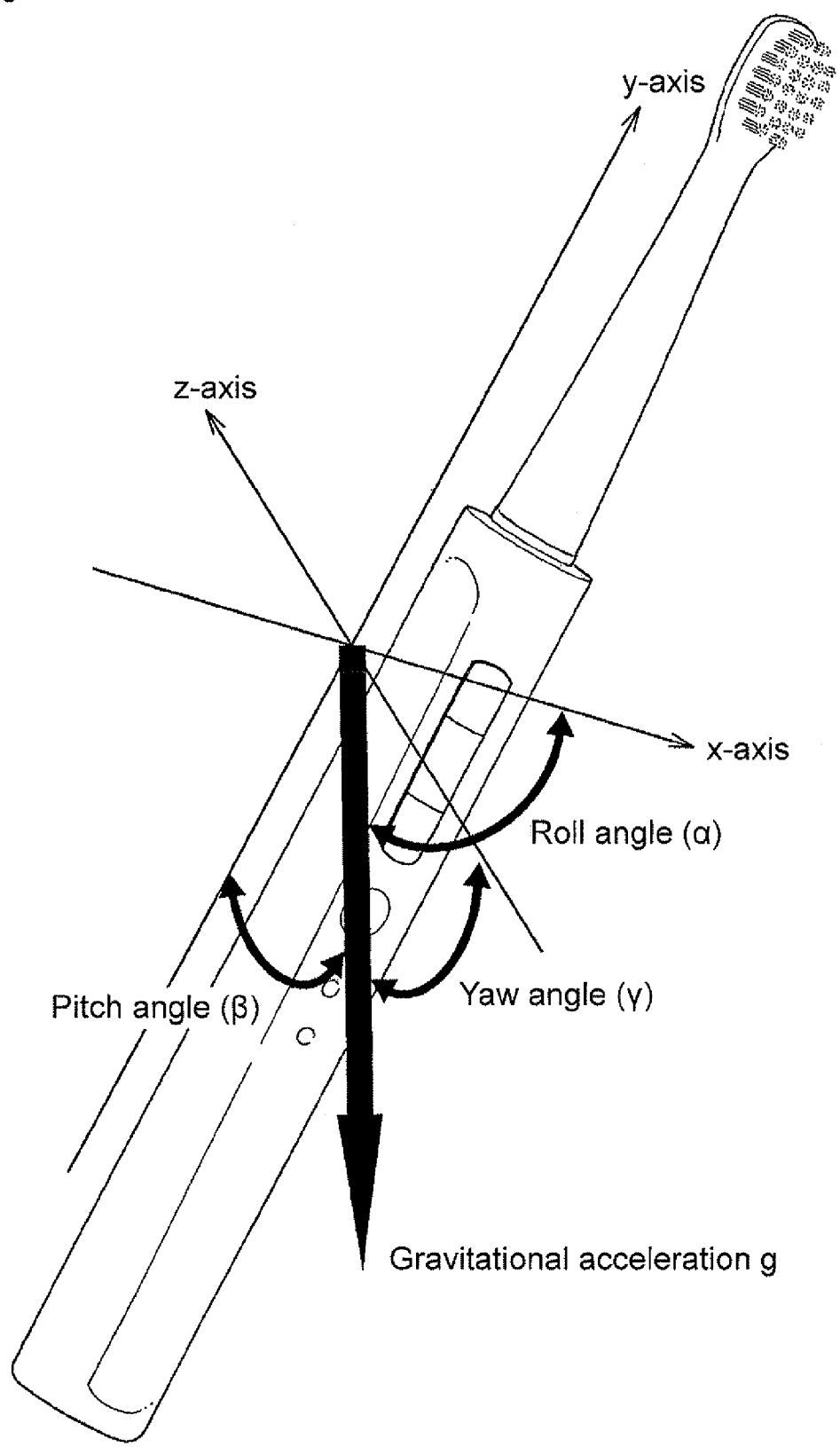
FIG. 30 is a view showing definition of a posture angle of the electric toothbrush.

The determination algorithm is only one example, and any determination algorithm may be used as long as the brushing part can be identified from the outputs Ax, Ay, Az of the acceleration sensor. For example, not only the values of Ax, Ay, Az are used as variables for determination straightaway, but also secondary variables obtained by appropriately combining Ax, Ay, Az may be used for the determination. The secondary variables can be arbitrarily set to be Ay/Az, Ax·Ax+Ay·Ay, Az−Ax, or the like, for example. Alternatively, after the acceleration information Ax, Ay, Az of the axes are converted into angle information (posture angles) α, β, γ as shown in FIG. 30, the brushing part may be determined. In the example of FIG. 30, an angle of the x-axis relative to the direction of the gravitational acceleration is defined as a roll angle α, an angle of the y-axis relative to the direction of the gravitational acceleration is defined as a pitch angle β, and an angle of the z-axis relative to the direction of the gravitational acceleration is defined as a yaw angle γ. Threshold values used for the determination can be determined from a result of a clinical experiment or the like.

(Measurement of Brushing Time)

FIG. 11 shows one example of the brushing information recorded in the memory. FIG. 11 is an example of a state where the part on the mandibular left buccal side is being brushed. Before the mandibular left buccal side, the part on the maxillary anterior buccal side is brushed for 7.5 seconds, and the part on the maxillary left buccal side is brushed for 12.2 seconds. The symbol "—" indicates that no data is recorded, that is, that part is not brushed yet.

In S30, the CPU 120 counts up the brushing time of the brushing part (on the mandibular left buccal side in the example of FIG. 11) estimated in S20. For example, when the processes S10 to S 50 in FIG. 6 are executed once in 0.1 second, the brushing time of the part on the mandibular left buccal side is counted up by +0.1 so as to be 2.1 seconds.

An accumulated value of the brushing time is recorded as the brushing information. That is, for example, in a case where the brushing part is moved to the maxillary left buccal side again, the brushing time stored in the memory is not reset but the brushing time is added to the stored value of 12.2 seconds.

(Estimation of Brush Angle)

In S40, the CPU 120 estimates the brush angle based on the posture detected in S10 (the output of the acceleration sensor), and updates the value of the brush angle of the current brushing part (on the mandibular left buccal side in the example of FIG. 11). At this time, the CPU 120 preferably calculates and records an average value of the brush angle from the value of the brush angle stored in the memory and an estimated value this time.

The brush angle is an application angle of the brush relative to a tooth axis (an axis along a head and a root of the tooth).

A view on the upper side of FIG. 12 shows a state where the brush angle is 15°, a view on the middle shows a state where the brush angle is 45°, and a view on the lower side shows a state where the brush angle is 90°. In order to effectively scrape out the food residue and the plaque from a periodontal pocket or a gap between the teeth, the brush may be moved so that tips of the brush are brought into the periodontal pocket and the gap between the teeth. Therefore, the brush angle is preferably within a range from 35 to 55°.

Figure 13:
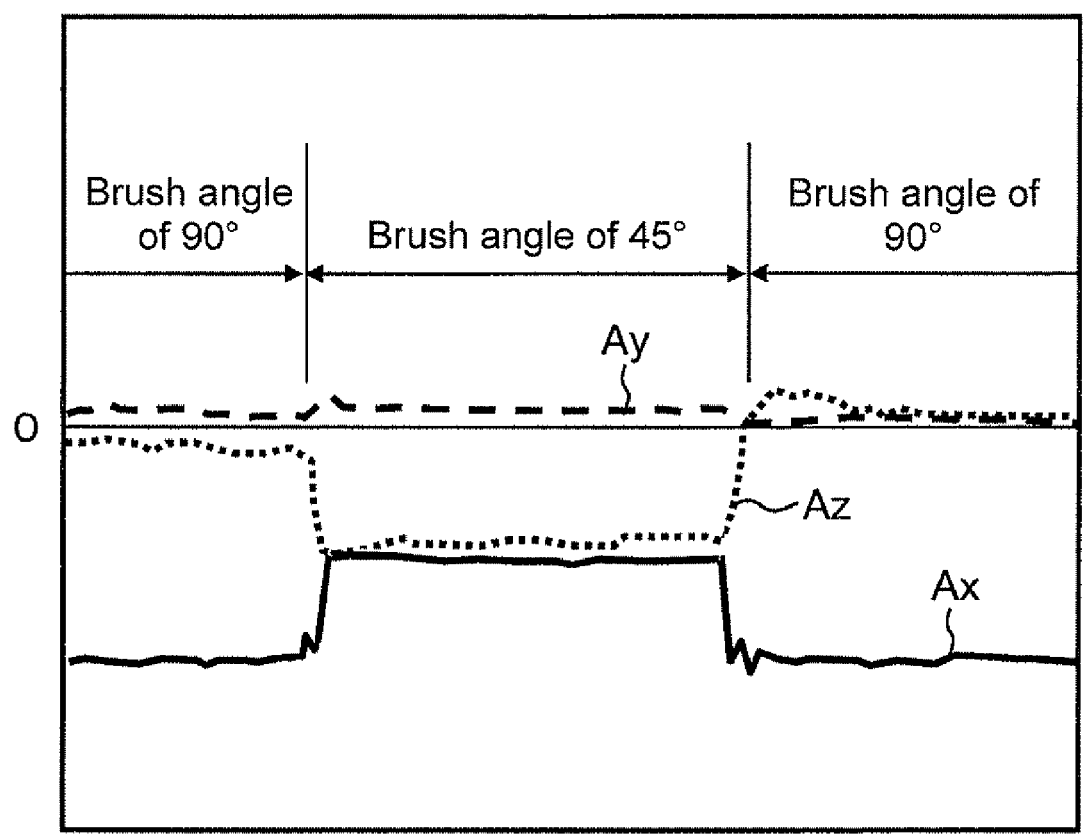
FIG. 13 is a graph showing a waveform change in the outputs of the sensor in accordance with a change in the brush angle.

The brush angle can be estimated from the acceleration component Az in the z direction, for example. This is because the value of Az is significantly changed in accordance with the brush angle. As shown in FIG. 13, Az is almost zero in a case where the brush angle is about 90°, and the value of Az is gradually increased as the brush angle is decreased. Since the acceleration component Ax in the x direction is also changed in accordance with the brush angle, preferably, the brush angle is estimated from Ax instead of Az, or the brush angle is estimated from both Ax and Az (the direction of the synthetic vector of Ax and Az). The brush angle may be calculated based on a continuous quantity or roughly estimated such as "less than 35°", "35 to 55°", and "not less than 55°".

(Detection of Brush Pressure)

In S50, the CPU 120 calculates the brush pressure based on outputs of the load sensor 17, and updates the value of the brush pressure of the current brushing part (on the mandibular left buccal side in the example of FIG. 11). At this time, the CPU 120 preferably calculates and records an average value of the brush pressure from the value of the brush pressure stored in the memory and a detected value this time.

When the brush pressure is too small, a scale removing force is lowered. On the contrary, when the brush pressure is too high, there is a possibility to cause a problem that the brush life is reduced, or a burden on the gum is increased. The brush pressure of the electric toothbrush may be smaller than a normal toothbrush. Thus, it is said that most people who have just started using the electric toothbrush tend to apply excessive brush pressure. An optimum value of the brush pressure is about 100 g.

(Evaluation and Output of Brushing Result)

The CPU 120 evaluates the brushing result for each part based on the brushing information recorded in the memory 121, and outputs an evaluation results to the display unit 110 (the display 111).

Figure 14:
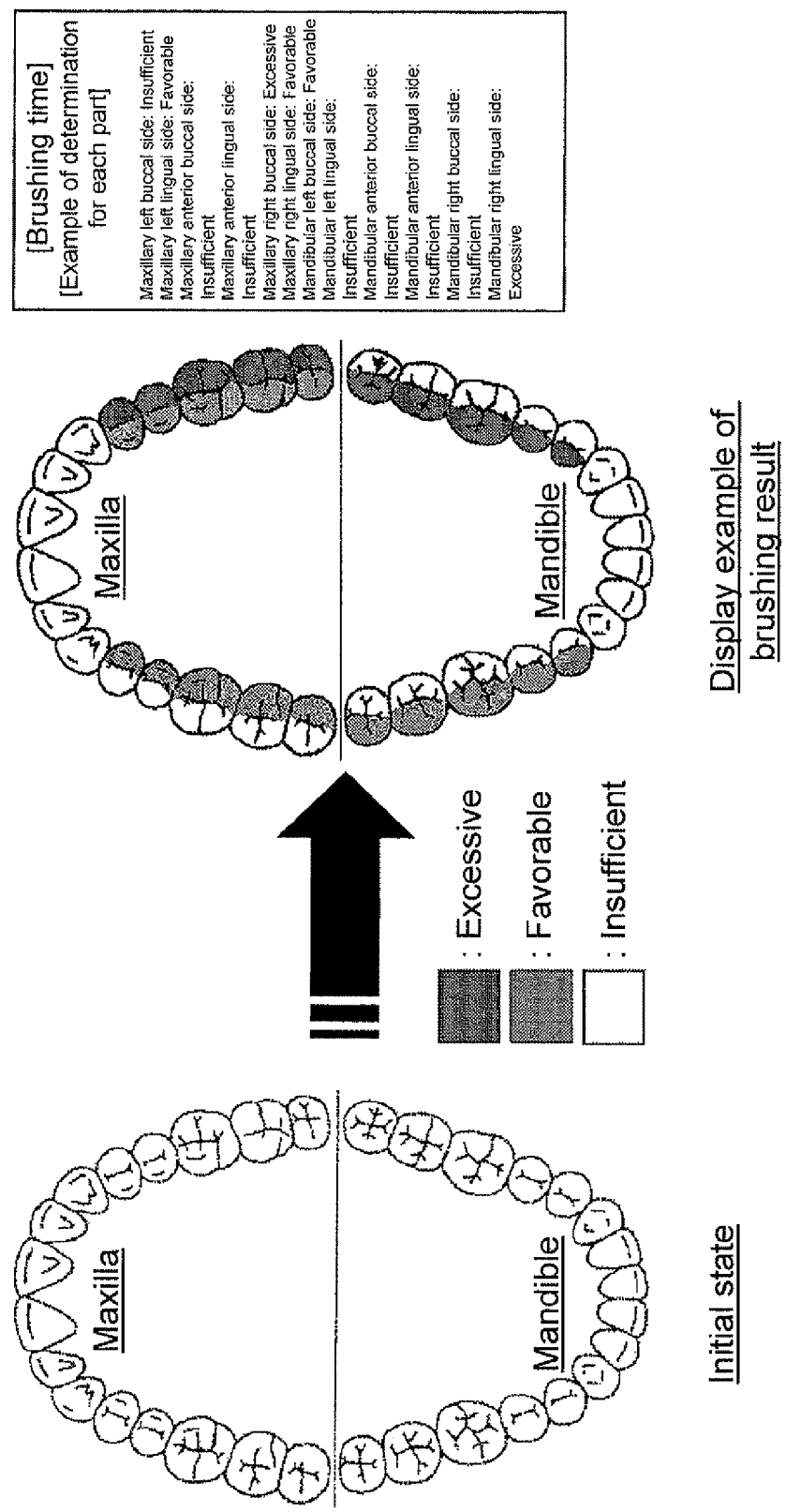
FIG. 14 is a view showing an output example of a brushing result (brushing time).

FIG. 14 is an output example of the evaluation result of the brushing time. The CPU 120 reads the brushing time for each part from the memory 121, and evaluates less-than-7-seconds as "Insufficient", 7-to-15-seconds as "Favorable", and over-15-seconds as "Excessive", for example. The evaluation result is sent to the indicator 110. The tooth row is drawn on the display 111 of the indicator 110, and the relevant part in the tooth row is lighted with a color in accordance with the evaluation result (for example, white for "Insufficient", yellow for "Favorable" and red for "Excessive"). By looking at such display, the user can quickly grasp for which part in the tooth row brushing is insufficient (or excessive).

Figure 15:
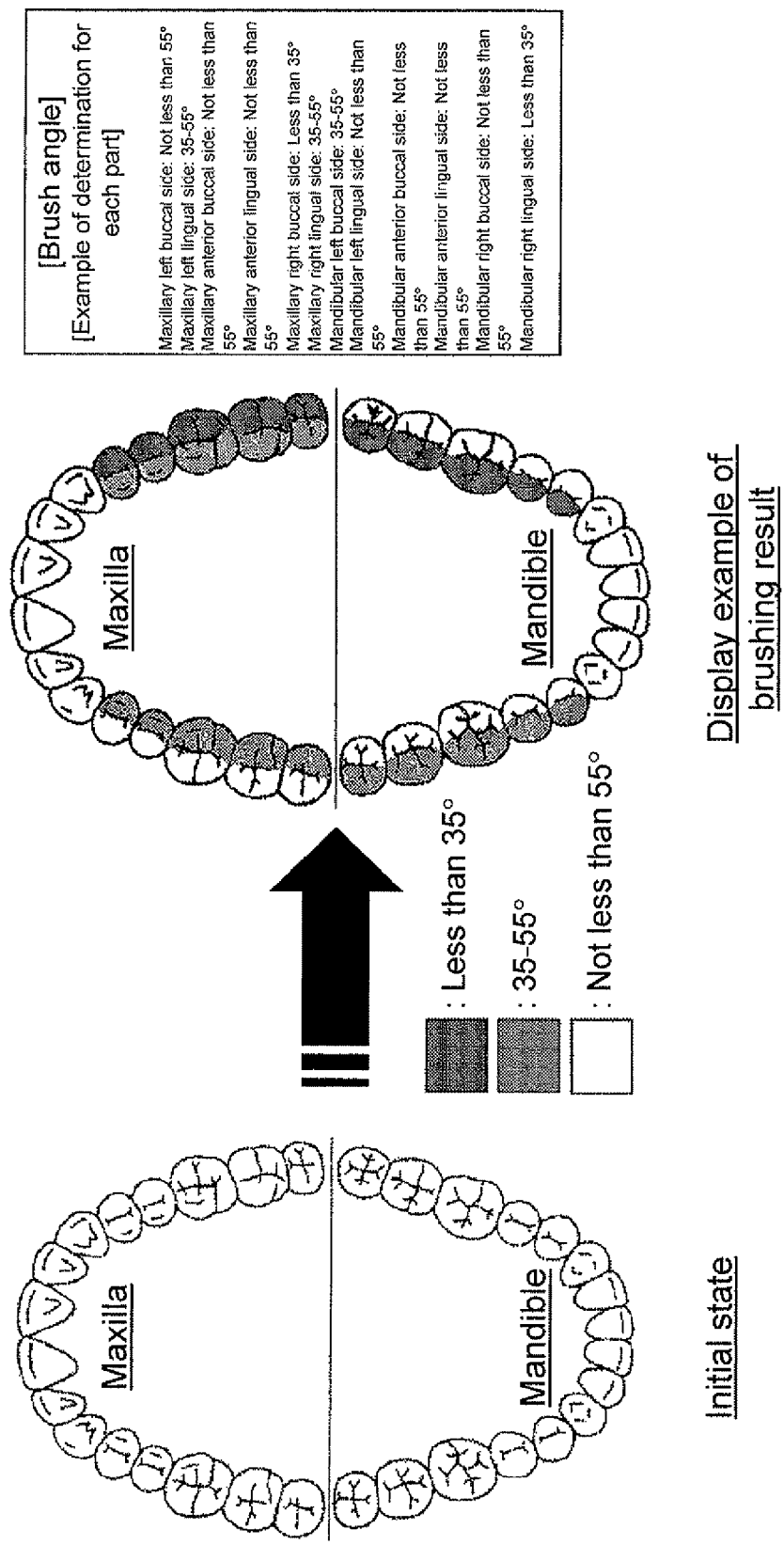
FIG. 15 is a view showing an output example of a brushing result (a brushing angle).

FIG. 15 is an output example of the evaluation result of the brush angle. For example, the brush angle is evaluated by three stages of "less than 35°", "35 to 55°", and "not less than 55°", for example, and each part in the tooth row is lighted with a color in accordance with the evaluation result. In a case where brushing is performed by an improper brush angle, the scale removing force is inferior to the optimum brush angle. Thus, there are possibilities that a desired brushing effect is not obtained and brushing takes time. When the evaluation of the brush angle for each part is outputted as in FIG. 15, the user can be aware of brushing by a correct brush angle.

Figure 16:
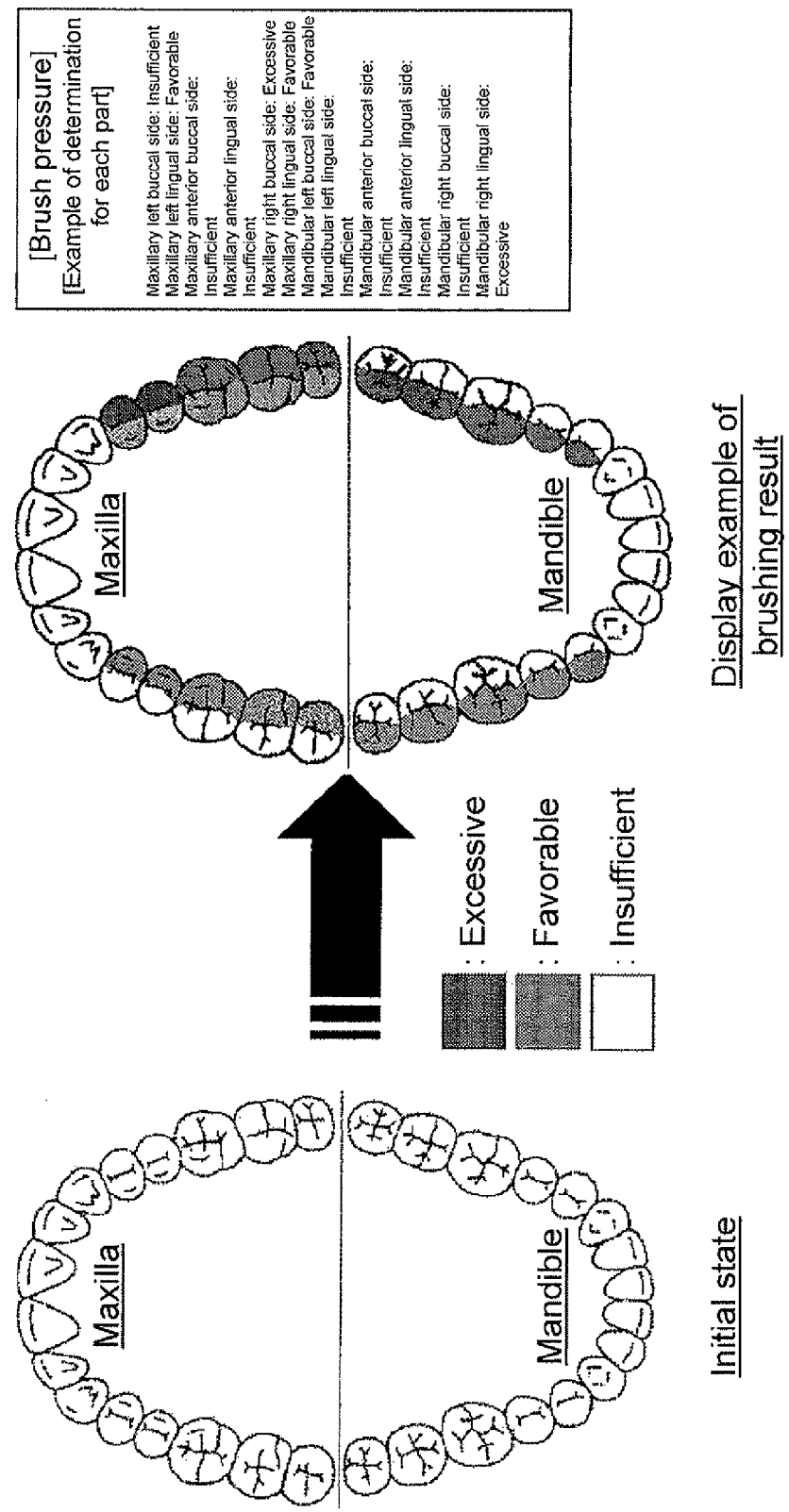
FIG. 16 is a view showing an output example of a brushing result (brushing pressure).

FIG. 16 is an output example of the evaluation result of the brush pressure. For example, less-than-80 g is evaluated as "Insufficient", 80-to-150 g is evaluated as "Favorable", and over-150 g is evaluated as "Excessive". Each part in the tooth row is lighted with a color in accordance with the evaluation result. When the brush pressure is improper as described above, there is a possibility to cause a problem that the scale removing force is lowered, the brush life is reduced, or the burden on the gum is increased. Nonetheless, it is difficult for the user to understand to what extent the force is added to obtain optimum brush pressure. In this regard, when the evaluation of the brush pressure for each part is outputted as in FIG. 16, the user can learn the proper brush pressure and also be aware of brushing by correct brush pressure.

Figure 17:
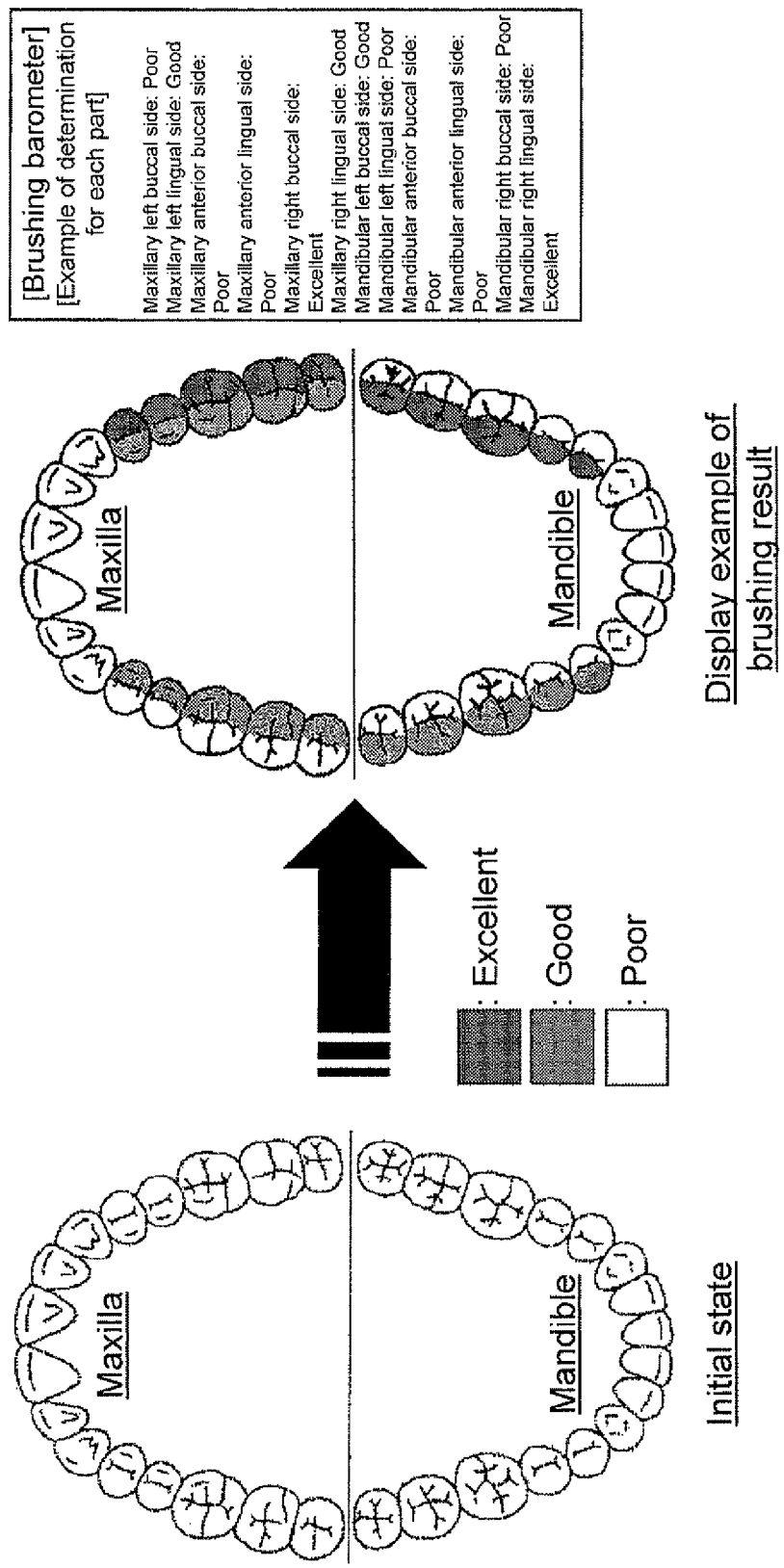
FIG. 17 is a view showing an output example of a brushing result (a brushing barometer).

FIG. 17 is an output example of the evaluation result of a brushing barometer. The brushing barometer indicates a barometer for comprehensively evaluating a plurality of evaluation items (the brushing time, the brush angle and the brush pressure) and shows an achievement degree of brushing. A calculation formula for the brushing barometer may be defined in any way. In the present embodiment, the brushing time and the brush pressure are respectively evaluated on a scale of 1 to 35, and the brush angle is evaluated on a scale of 1 to 30. The sum of the evaluation values (a scale of 1 to 100) is used as the brushing barometer. In the example of FIG. 17, not-less-than-80 is evaluated as "Excellent", 60-to-80 is evaluated as "Good", and less-than-60 is evaluated as "Poor". By outputting such comprehensive evaluation, a more useful guideline can be given to the user.

With the configuration of the present embodiment described above, by utilizing the outputs of the acceleration sensor, the posture of the brush can be highly precisely determined, and the brushing part can be identified with higher precision and more resolution capability than the conventional art. Therefore, the brushing result for the part more finely divided than the conventional art can be evaluated, and a highly useful and reliable evaluation guideline can be provided to the user. Moreover, since the acceleration sensor is small in size, there is an advantage that the acceleration sensor can be easily assembled into the electric toothbrush main body.

The evaluation results of FIGS. 14 to 17 may be displayed on the display 111 at the same time or displayed one by one. In the latter case, the display may be switched automatically or by a button operation of the user.

In the above embodiment, the result is automatically displayed when the power supply of the toothbrush is turned OFF. However, it is assumed that brushing is performed at place which is different from place where the indicator is installed. Thus, for example, a function of sending the brushing information from the toothbrush main body to the indicator when the user pushes a button provided in the indicator or the toothbrush main body and displaying the result on the indicator is preferably provided.

The brushing information and the evaluation result accumulated in the memory may be printed out. For example, a printer may be mounted in the charger or the indicator, or print data may be sent from the toothbrush main body, the charger or the indicator to an external printer. A function of forwarding data of the brushing information and the evaluation results to an external device (a personal computer, a cellular phone, a PDA or the like) by wireless communication or wire communication is also preferable. A memory card slot may be provided in the toothbrush main body, the charger, the indicator or the like so that the data of the brushing information and the evaluation results can be recorded in an external memory card.

The optimum values (target values) of the brushing time, the brush angle and the brush pressure may be set differently for each part. For example, for a tooth surface (a side surface) of the molar tooth, the brush angle of 35 to 55° is preferable in order to effectively scrape out the food residue and the plaque from the periodontal pocket and the gap between the teeth with the tips of the brush. Meanwhile, for the front tooth having a relatively large tooth surface, an angle larger than the above brush angle (such as 55 to 90°) is preferable. The brush angle is favorably about 0° for an occlusal surface of the molar tooth. Further, the optimum brushing time, brush angle and brush pressure can be determined not from the view of a brushing effect but from the view of avoiding damage to a tissue such as the gum. When the optimum values are set for each part and the evaluation is performed, a more highly useful and reliable evaluation guideline can be provided.

(Second Embodiment)

Figure 18:
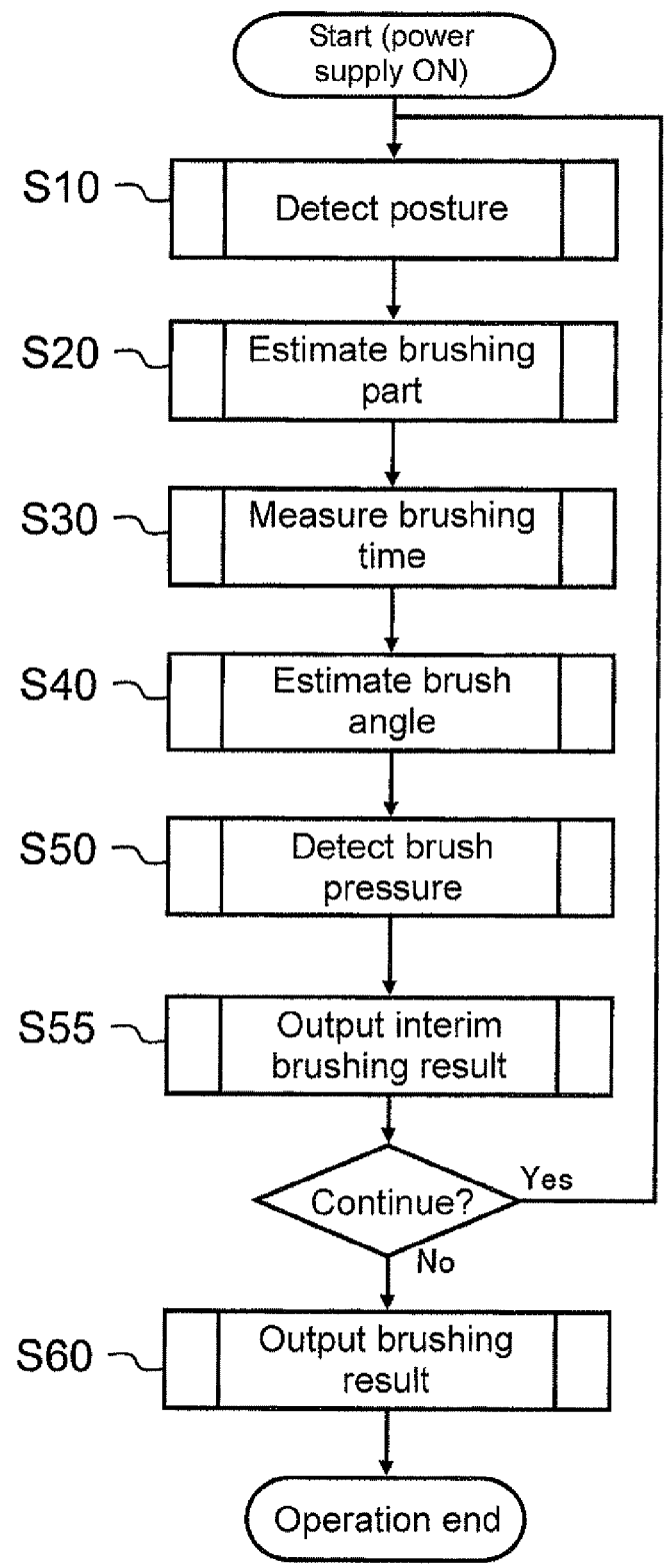
FIG. 18 is a flowchart showing a main routine of a brushing evaluation process of a second embodiment.

FIG. 18 is a flowchart of a brushing evaluation process of a second embodiment. The brushing result is outputted after completion of brushing in the first embodiment, whereas interim results are outputted in the middle of brushing in the second embodiment (S55). Other configurations are the same as the first embodiment.

According to processes of the present embodiment, brushing can be performed while confirming progress of the brushing time and the brushing barometer (the achievement degree) in real-time. Thus, convenience is improved. By confirming the evaluation results of the brush angle and the brush pressure, the user can determine whether or not the brush angle and the brush pressure are proper. In the second embodiment, a function of outputting the interim result of the brush angle corresponds to brush angle guide means of the present invention.

(Third Embodiment)

Figure 19:
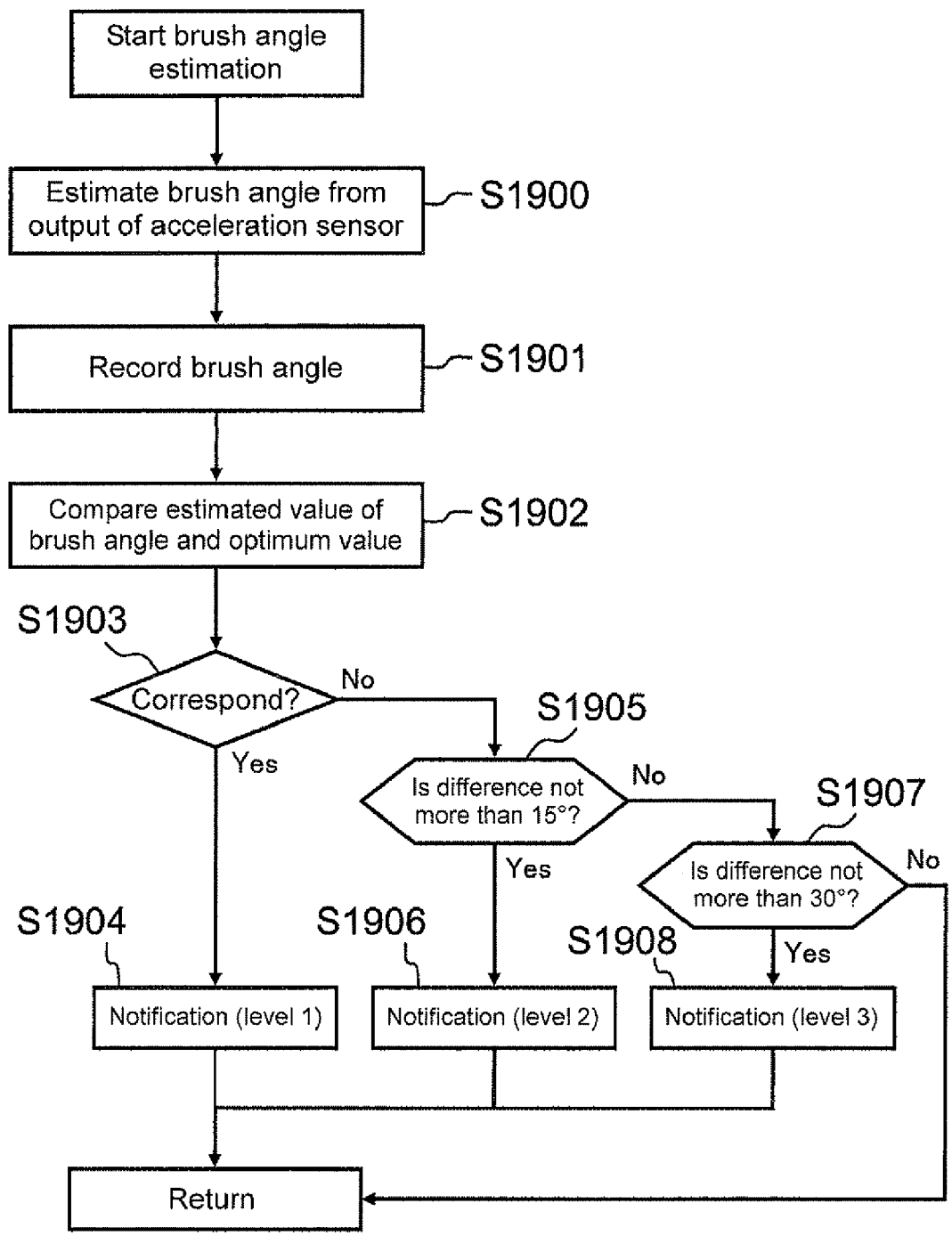
FIG. 19 is a flowchart of a brush angle estimation process of a third embodiment.

FIG. 19 is a flowchart of a brush angle estimation process (S40 of FIG. 5) of a third embodiment. In the present embodiment, the CPU 120 estimates the brush angle, and then, if necessary, outputs a guide for informing the user of whether or not the brush angle is proper.

The CPU 120 firstly estimates the brush angle based on a posture vector A obtained from the acceleration sensor (particularly the acceleration component Az in the z direction) (S1900). The CPU 120 updates the value of the brush angle for the current brushing part estimated in S20 (S1901). At this time, the CPU 120 preferably calculates and records the average value of the brush angle from the value of the brush angle stored in the memory and an estimated value this time.

Next, the CPU 120 compares the estimated value of the brush angle and the optimum value of the brush angle in the current brushing part (S1902). For example, given that the optimum value of the brush angle is "35 to 55°", in a case where the estimated value of the brush angle is within the above range (S1903; YES), notification (guide) of level 1 is outputted (S1904). In a case where a difference between the estimated value of the brush angle and the optimum value is not more than 15° (that is, the estimated value is 20 to 35° or 55 to 70°) (S1905; YES), notification of level 2 is outputted (S1906). In a case where the difference between the estimated value and the optimum value is not more than 30° (that is, the estimated value is 5 to 20° or 70 to 85°) (S1907; YES), notification of level 3 is outputted (S1908). In a case where the difference is more than 30°, no notification is outputted (S1907; NO).

Figure 20:
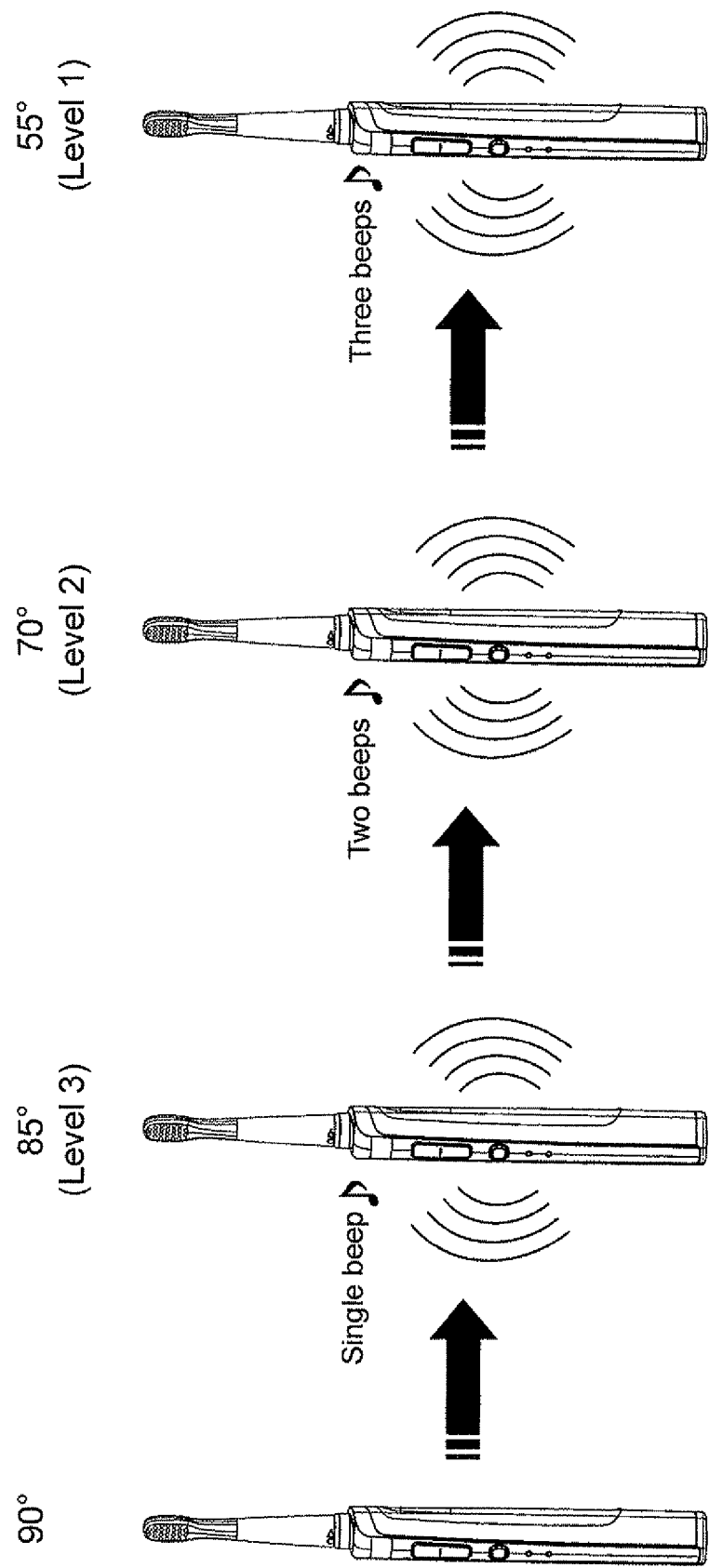
FIG. 20 is a view showing an example of a change in a notification alert in accordance with the brush angle.

FIG. 20 shows an example of a change in a notification alert in accordance with the brush angle. In a state where the brush angle is 90°, no notification is outputted. When the brush is gradually rotated, a single beep serving as a notification alert of level 3 is outputted at a time point when the brush angle is 85°. When the brush is further rotated, two beeps serving as a notification alert of level 2 is outputted at a time point when the brush angle is 70°, and three beeps serving as a notification alert of level 1 is outputted at a time point when the brush angle is 55° which is the optimum value.

The user can grasp that the brush angle comes close to the optimum value by such a change in the notification alert, and hence the brush angle can easily correspond to the optimum value. Since the operation is quick and enjoyable, the toothbrush is useful as a learning tool for teaching children the correct brush angle.

Light, vibration and voice can be used as a method of the notification in addition to sound. In a case of light, a color or a blinking pattern may be changed in accordance with the level. In a case of vibration, strength and length of vibration may be changed in accordance with the level. In a case of voice, messages such as "tilt the toothbrush by about 30° more", "tilt the toothbrush little more", and "this is the optimum brush angle" may be notified.

In the present embodiment, the notification that the brush angle is the optimum value is outputted. On the contrary, no notification may be outputted when the brush angle is the optimum value and notification (a caution) may be outputted when the brush angle is apart from the optimum value.

(Fourth Embodiment)

Figure 21:
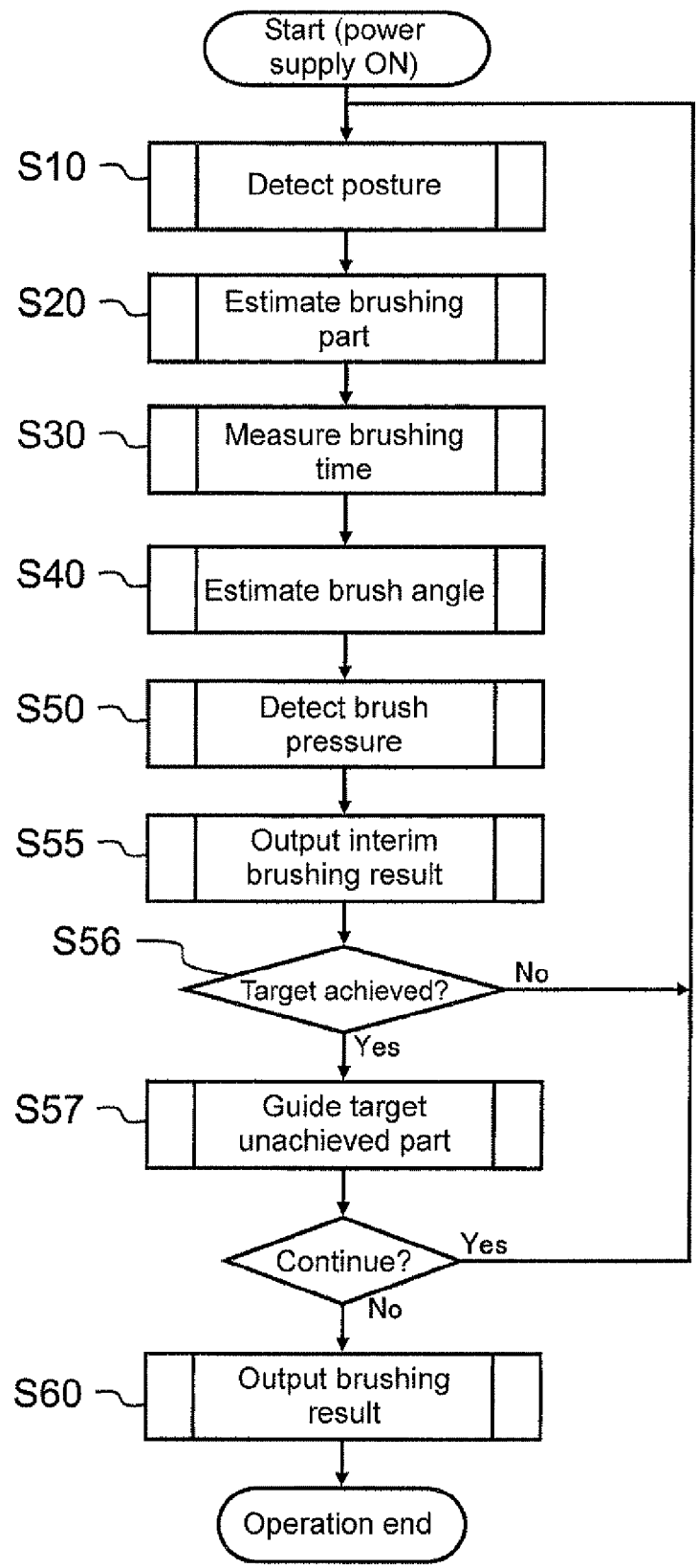
FIG. 21 is a flowchart showing a main routine of a brushing evaluation process of a fourth embodiment.

FIG. 21 is a flowchart of a brushing evaluation process of a fourth embodiment. This embodiment is different from the second embodiment in terms that a process for determining and guiding a part to be brushed next based on the brushing result for each part (S56, S57) is added. Other configurations are the same as the second embodiment.

When the brushing result for the current brushing part is updated in the processes S10 to S55, the CPU 120 determines whether or not a brushing target is achieved for the current brushing part (S56). For example, the CPU may determine whether or not the target is achieved by determining whether or not the brushing time reaches 10 seconds, whether or not the brushing barometer exceeds 80, or the like. In a case where the target is unachieved (S56; NO), brushing for the current brushing part should be continued and hence the flow is returned to the process S10. In a case where the target is achieved (S56; YES), brushing for the current brushing part is completed and other parts are to be brushed, and hence the flow is advanced to the process S57.

In S57, the CPU 120 refers to the brushing result for each part and selects a target unachieved part (that is, a part not sufficiently brushed yet). In a case where there is a plurality of target unachieved parts, a part to which the toothbrush is easily moved from the current brushing part is determined to be the part to be brushed next. In general, it is said that moving the brush continuously without detaching the brush from the teeth is effective for leaving no unbrushed part. Thus, for example, pattern data defining the brushing order of continuous brush movement such as the order "from the maxillary left buccal side, the maxillary anterior buccal side, the maxillary right buccal side, the mandibular right buccal side, the mandibular anterior buccal side, the mandibular left buccal side, the mandibular left lingual side, the mandibular anterior lingual side, the mandibular right lingual side, the maxillary right lingual side, the maxillary anterior lingual side, to the maxillary left lingual side" is prepared in advance, and the part to be brushed next may be determined in accordance with this brushing order. The CPU 120 displays the determined part to be brushed next on the indicator 110. For example, the relevant part in the tooth row may be blinked or lighted with a predetermined color.

With such a guide, brushing can be efficiently performed without leaving the unbrushed part. That is, the part to be brushed next is selected from the parts not sufficiently brushed yet. Thus, the unbrushed part is not left and useless actions such as brushing the same part repeatedly are eliminated. In the toothbrush of the present embodiment, the part being actually brushed is identified. Thus, even in a case where the user brushes another part against the guide, the brushing result can be correctly recorded and evaluated, and the guide for the brushing order can be appropriately corrected.

Figure 22:
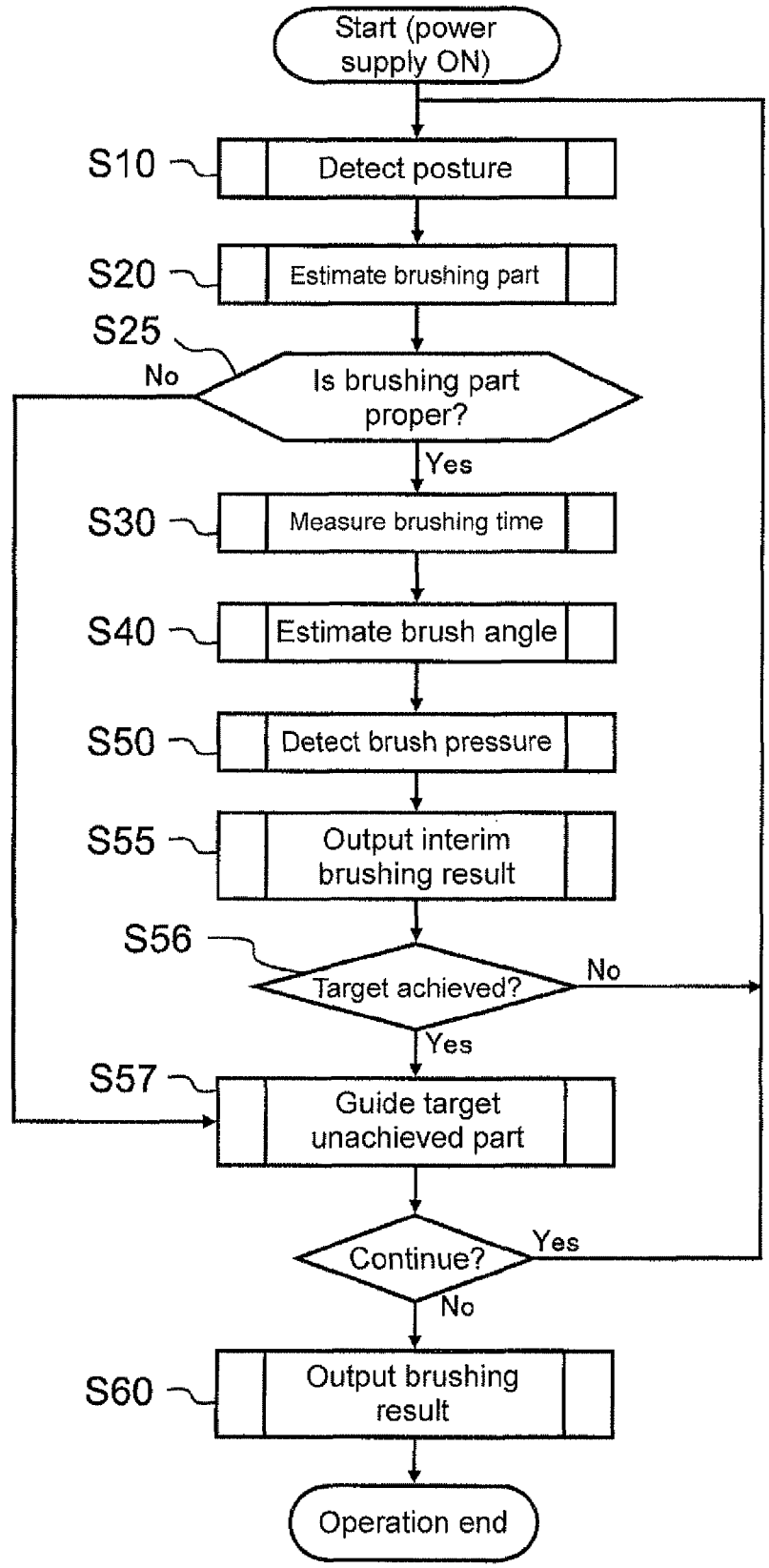
FIG. 22 is a modified example of the flowchart in FIG. 21.

The CPU 120 can determine whether or not the user is brushing the part following the guide. For example, as shown in a flowchart of FIG. 22, after estimating the current brushing part (S20), the CPU 120 determines whether or not the current brushing part is proper (S25). In a case where the part is different from the part to be brushed (S25; NO), a change in the brushing part may be guided (S57). In a case where the user is to brush an already-brushed part repeatedly or the like, the change in the brushing part is encouraged. Thus, brushing can be efficiently performed.

(Fifth Embodiment)

Figure 23:
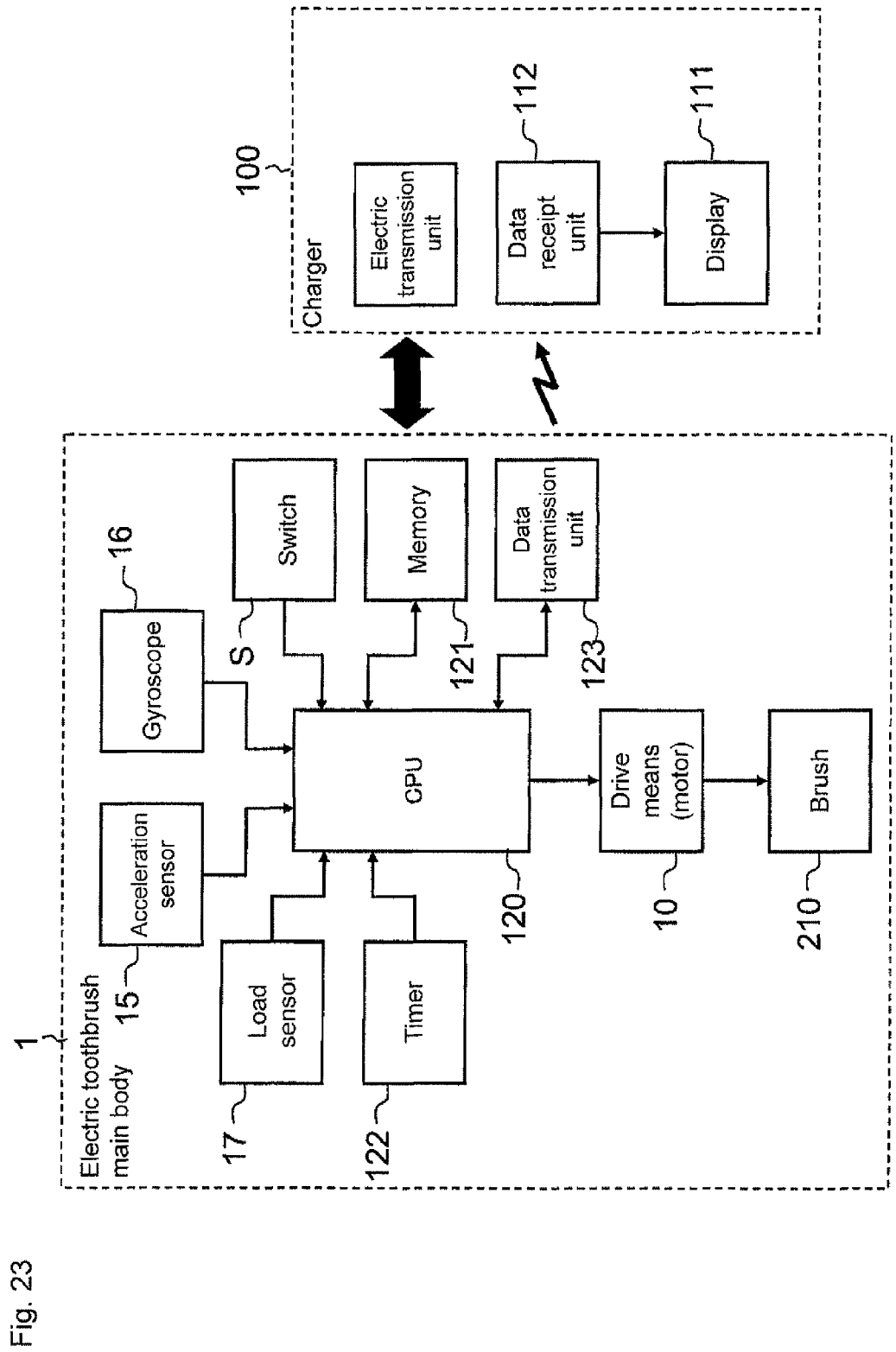
FIG. 23 is a block diagram of an electric toothbrush of a fifth embodiment.
Figure 24:
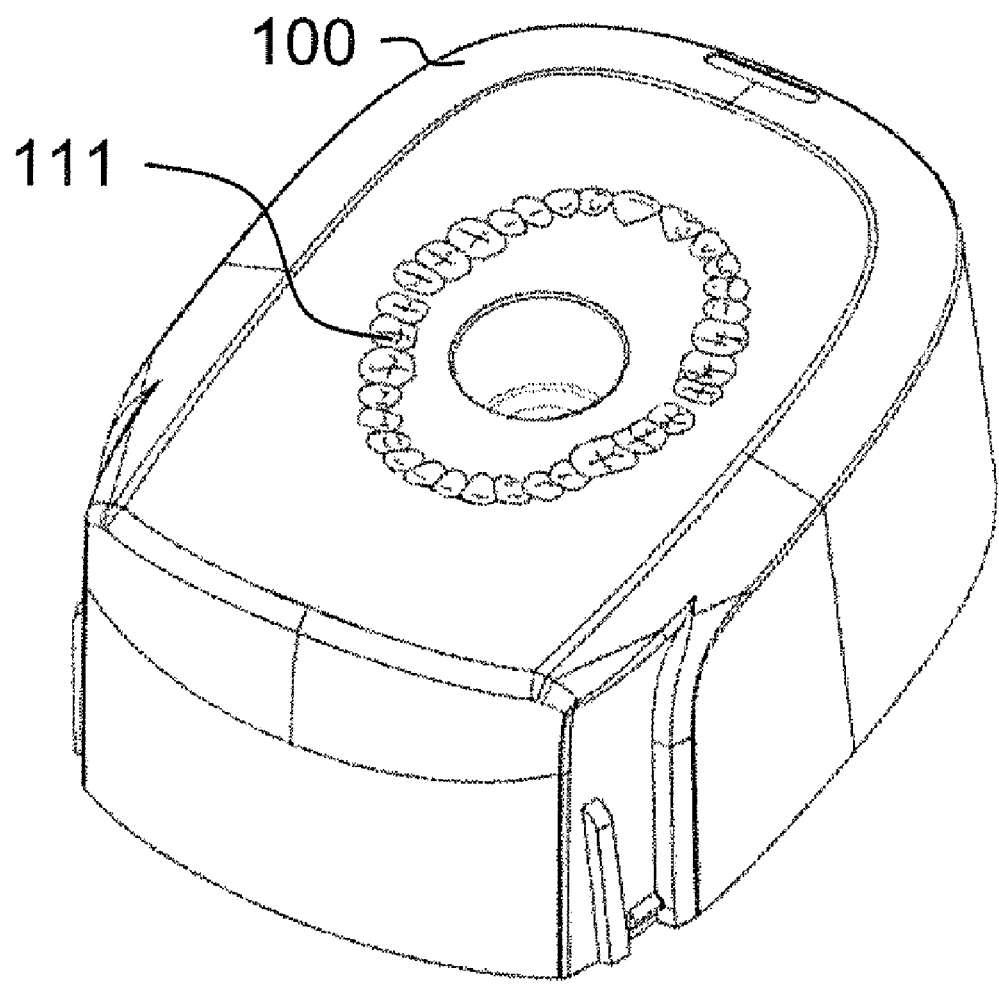
FIG. 24 is a perspective view showing an outer appearance of a charger of the fifth embodiment.

FIG. 23 is a block diagram of an electric toothbrush of a fifth embodiment. The electric toothbrush of the present embodiment is provided with a multi-axis (three-axis herein) gyroscope 16 inside the main body 1. The display 111 and the data receipt unit 112 are provided in the charger 100. FIG. 24 is a perspective view showing an outer appearance of the charger 100 of the fifth embodiment. This display 111 may be formed by a liquid crystal panel or a light emitting element such as a LED.

The gyroscope 16 is installed so as to detect the angular rate about the z-axis, the angular rate about the x-axis, and the angular rate about the y-axis. Any type of gyroscope including a vibrating gyroscope, an optical gyroscope and a mechanical gyroscope can be utilized as the gyroscope 16. However, a MEMS sensor can be favorably used by reason that the MEMS sensor is small in size so as to be easily assembled into the main body 1. Not a rate gyro for outputting the angular rate but a rate integrating gyro or a posture gyro for outputting the angle may be utilized. In order to eliminate noise due to vibration of the brush (such as a frequency component of about 100 to 300 Hz serving as a drive frequency of the brush), the band pass filter may be used for outputs of the gyroscope.

When the toothbrush main body 1 is in a static state (for example, in a state where the brush is continuously applied to one brushing part), the outputs of the acceleration sensor 15 only essentially include gravitational acceleration components. In this case, the three-dimensional posture of the brush can be accurately detected. Thus, the brushing part and the brush angle can be precisely estimated. However, when the toothbrush main body 1 is in a movement state (for example, when the brush is moved from a brushing part to another brushing part), the outputs of the acceleration sensor 15 can include not only the gravitational acceleration components but also dynamic acceleration components. The dynamic acceleration components are unnecessary signal components (noise) upon calculating the three-dimensional posture. Meanwhile, the outputs of the gyroscope 16 are not observed when the toothbrush main body 1 is in a static state. Only when the toothbrush main body 1 is being moved, significant signals are outputted. By utilizing such a difference in characteristics of the sensors, in the present embodiment, the three-dimensional posture of the toothbrush is detected based on both the outputs of the acceleration sensor 15 and the gyroscope 16.

Specifically, in the posture detection process (S10), the CPU 120 firstly obtains the outputs of the acceleration sensor 15 and the outputs of the gyroscope 16. When absolute values of the outputs of the gyroscope 16 are less than predetermined threshold values, the CPU 120 regards the toothbrush main body 1 as static, and determines the three-dimensional posture from the outputs Ax, Ay, Az of the acceleration sensor 15. When any of the absolute values of the outputs of the gyroscope 16 is not less than the predetermined threshold value, the CPU 120 estimates the dynamic acceleration components in the x, y and z directions from the outputs of the gyroscope 16, and corrects the values of Ax, Ay, Az. Thereby, the dynamic acceleration components included in Ax, Ay, Az are canceled, and the three-dimensional posture of the brush can be precisely calculated.

Instead of correcting the outputs of the acceleration sensor by using the outputs of the gyroscope, the posture of the brush may be not detected in a case where the outputs of the gyroscope are obtained. That is, only when the outputs of the gyroscope are less than the predetermined threshold values, the processes including the posture detection, the brushing part estimation, the brushing time measurement, the brush angle estimation, and the brush pressure detection. Thereby, only when the posture estimated from the outputs of the acceleration sensor is reliable to some extent, the brushing result is recorded and evaluated.

An angle change amount $\Delta\theta yz$ about the x-axis, an angle change amount $\Delta\theta zx$ about the y-axis, and an angle change amount $\Delta\theta xy$ about the z-axis may be calculated from the outputs of the gyroscope, and a posture vector A'=(Ax', Ay', Az') obtained in the posture detection process one-clock before may be rotated by the angle ($\Delta\theta yz$, $\Delta\theta zx$, $\Delta\theta xy$), thereby calculating the current posture vector A=(Ax, Ay, Az). The posture of the electric toothbrush may be calculated and evaluated by the angle information of the roll angle $\alpha$, the pitch angle $\beta$, and the yaw angle $\gamma$ (refer to FIG. 30), instead of the acceleration information Ax, Ay, Az.

With the configuration of the present embodiment described above, the three-dimensional posture of the electric toothbrush can be highly precisely determined by combining the outputs of the acceleration sensor and the gyroscope (including selecting of any of the outputs of the acceleration sensor and the gyroscope according to conditions). In a case of an electric toothbrush with the bass method requiring many translation motions, posture information with sufficient precision can be obtained even by combination of the acceleration sensor and the band pass filter. However, in a case of the rolling method, three-dimensional undulation of the toothbrush main body is generated. Thus, an error factor is large only with the acceleration information, and there is a fear that precision of the posture detection is lowered. In such a case, the method of the present embodiment for utilizing angular rate information of the gyroscope is effective.

(Sixth Embodiment)

Figure 25:
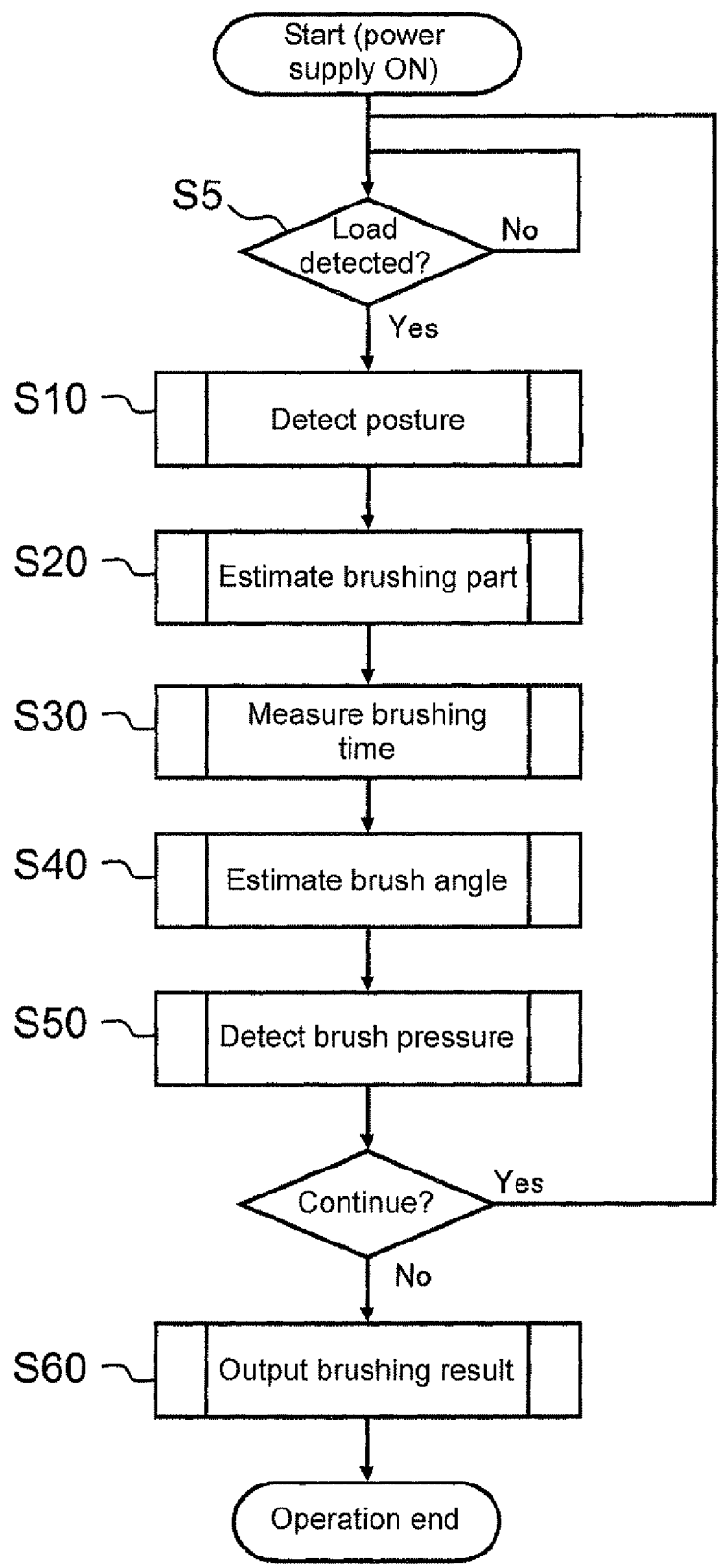
FIG. 25 is a flowchart showing a main routine of a brushing evaluation process of a sixth embodiment.

FIG. 25 is a flowchart of a sixth embodiment. In the present embodiment, the CPU 120 firstly determines whether or not the load is imposed on the brush based on the outputs of the load sensor 17 (S5). For example, when output values of the load sensor 17 exceed predetermined threshold values, the CPU 120 may regard as "the load is imposed on the brush". Until the load is imposed on the brush, the following processes are in a standby state (S5; NO).

When the load is not imposed on the brush, the brush is highly possibly being moved between the parts. Since the posture of the brush is largely changed during movement, estimation precision of the brushing part is lowered, and in the first place, it is not right to record and evaluate the brushing time, the brush angle and the like during movement. Thus, as in the present embodiment, while the load is not imposed on the brush, the processes such as the posture detection, the brushing part estimation, the brushing time measurement, the brush angle estimation, the brush pressure detection, and brushing result output are inhibited, thereby omitting useless processes and also improving reliability in the estimation precision and the evaluation.

(Seventh Embodiment)

Figure 26:
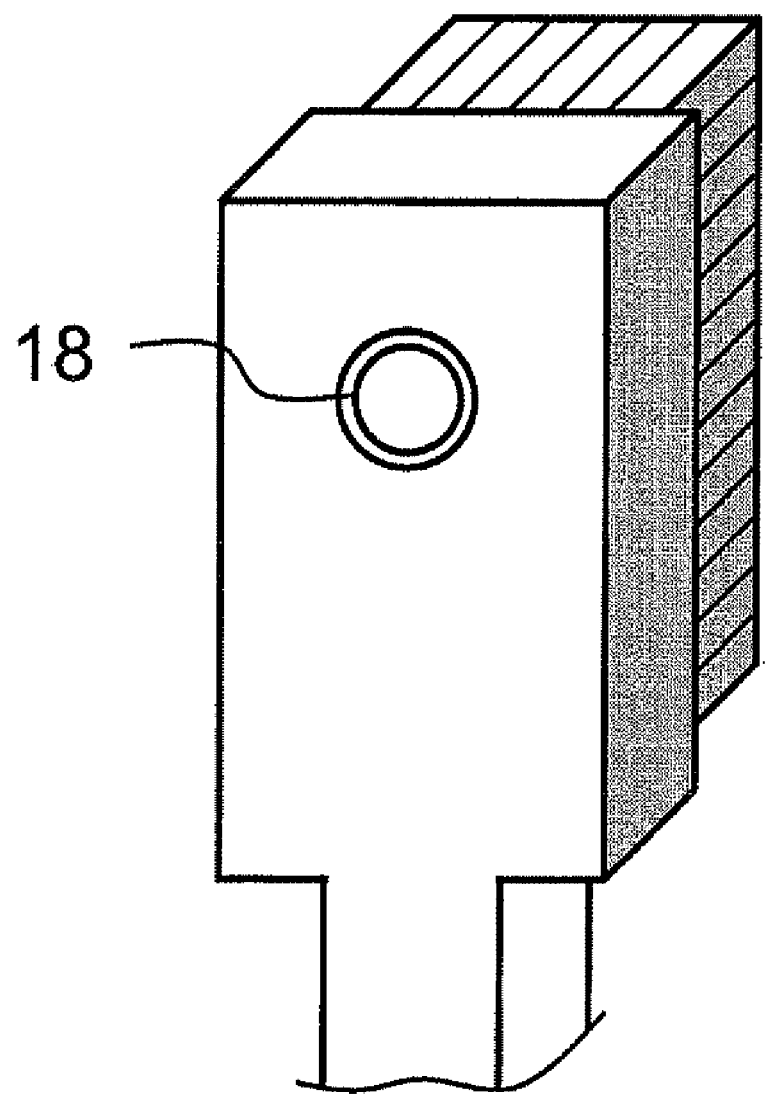
FIG. 26 is a perspective view showing a brush part of an electric toothbrush of a seventh embodiment.

FIG. 26 shows a brush part of an electric toothbrush of a seventh embodiment. The electric toothbrush of the present embodiment is provided with a temperature sensor 18 for detecting a temperature of the brush part. The temperature sensor 18 is installed on a back surface of the brush. Any type of sensor including an infrared ray sensor and a thermistor can be utilized as the temperature sensor 18.

Figure 27:
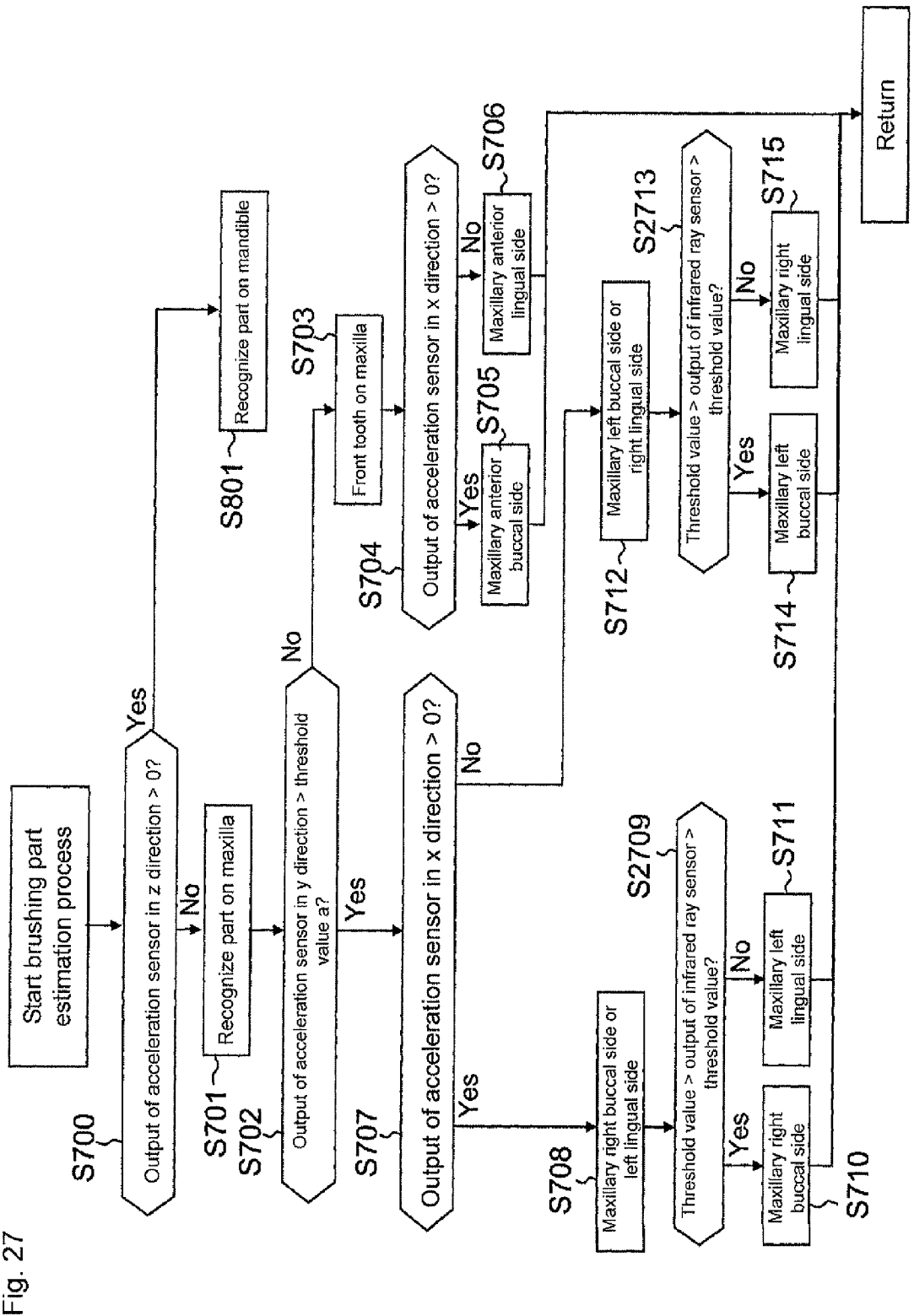
FIG. 27 is a flowchart of a brushing part estimation process (the maxilla) of the seventh embodiment.
Figure 28:
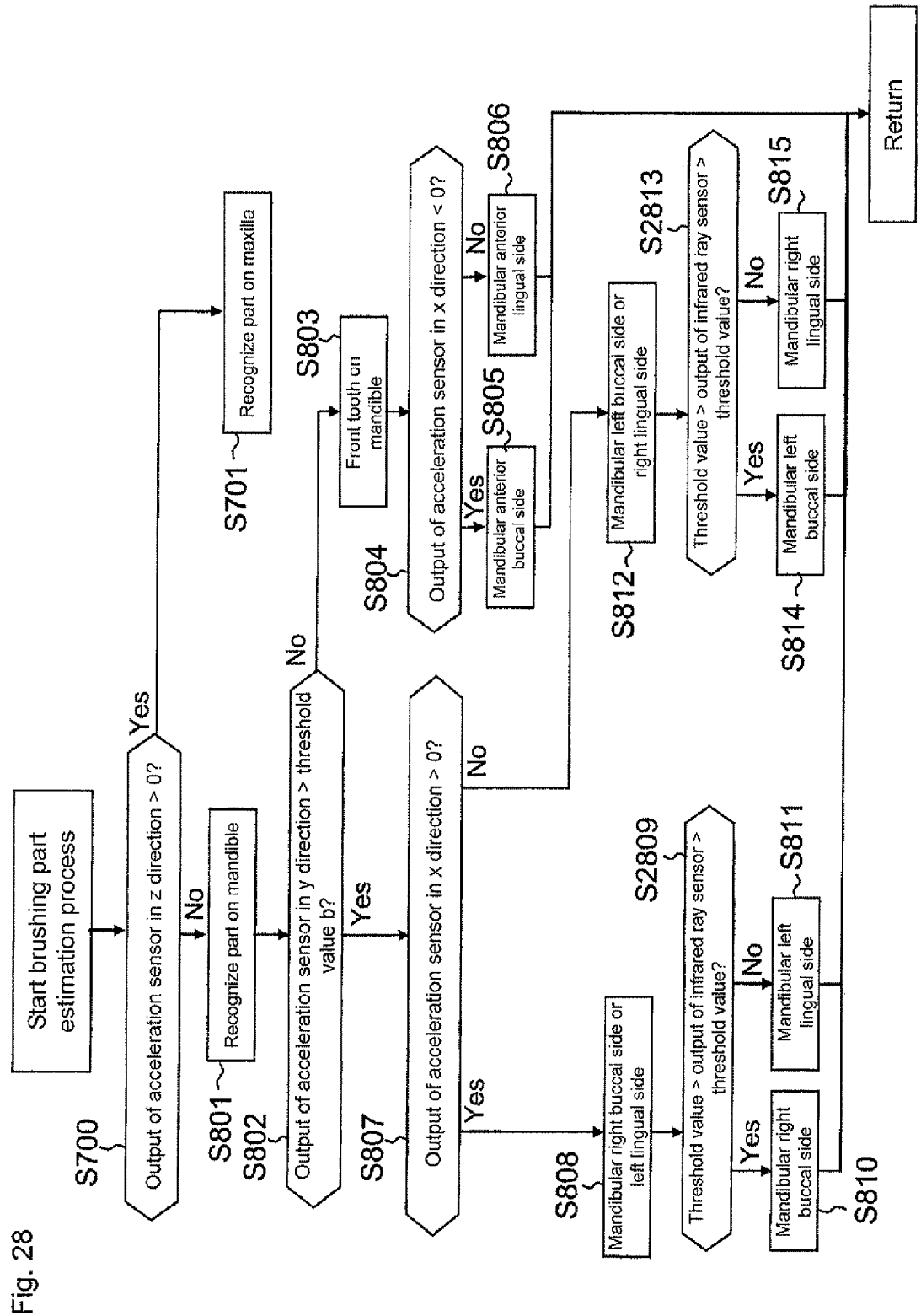
FIG. 28 is a flowchart of a brushing part estimation process (the mandible) of the seventh embodiment.

FIGS. 27 and 28 are flowcharts of brushing part estimation processes (S20). The processes are different from the brushing part estimation processes of the first embodiment (FIGS. 7 and 8) in terms that the buccal side and the lingual side are distinguished based on an output of the temperature sensor 18.

In the process of the maxilla in FIG. 27, after determining the "maxillary left buccal side or maxillary right lingual side" based on the outputs of the acceleration sensor 15 (S708), the CPU 120 determines whether or not an output value of the temperature sensor 18 is within a predetermined range (S2709). When the brush is on the buccal side, the temperature sensor 18 comes into contact with or comes close to the back side of a cheek. Thus, the output value close to a body temperature can be obtained. Meanwhile, when the brush is on the lingual side, the temperature sensor 18 comes into contact with the outside air. Thus, the output value lower than the body temperature can be obtained. Therefore, for example, the CPU 120 determines the part on the "maxillary right buccal side" in a case where the output value of the temperature sensor 18 is within a range from 36 to 38 degrees (S710), and determines the part on the "maxillary left lingual side" in other cases (S711). Similarly, the "maxillary left buccal side" and the "maxillary right lingual side" can be distinguished based on the output value of the temperature sensor 18 (S2713). Similarly in the process of the mandible, the "mandibular left lingual side" and the "mandibular right buccal side" can be distinguished (S2809) and the "mandibular right lingual side" and the "mandibular left buccal side" can be distinguished (S2813) based on the output value of the temperature sensor 18.

(Eighth Embodiment)

Figure 31:
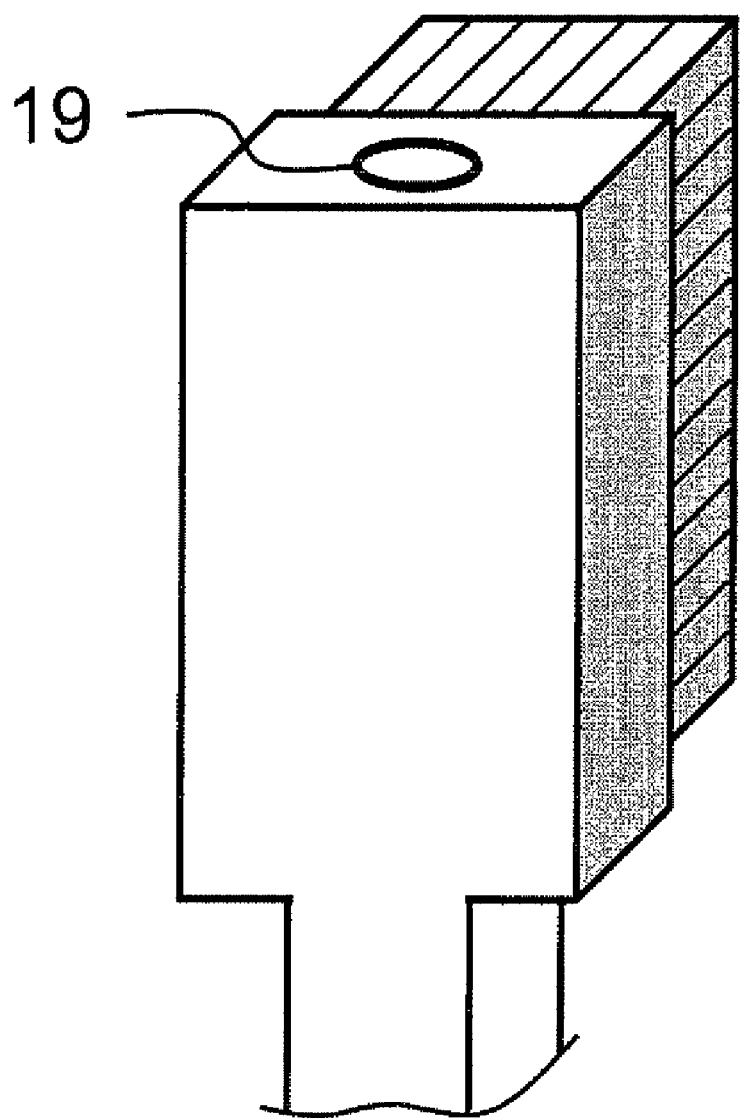
FIG. 31 is a perspective view showing a brush part of an electric toothbrush of an eighth embodiment.

FIG. 31 shows a brush part of an electric toothbrush of an eighth embodiment. In the seventh embodiment, temperature information by the temperature sensor 18 is utilized for identifying the brushing part (distinguishing the buccal side and the lingual side). However, in this seventh embodiment, image information is utilized.

As shown in FIG. 31, a camera 19 is provided in a front end of a brush head in the y direction. Any camera including a visible-light camera and an infrared ray camera can be utilized as the camera 19 as long as the camera is capable of obtaining the image information in the oral cavity. The infrared ray camera is to monitor radiated heat (also called as a thermograph). Since there is a possibility that it is dark in the oral cavity during brushing, it can be said that the infrared ray camera is preferred to the visible-light camera. In the present embodiment, it is sufficient to see a profile of uvula as described below. Thus, a resolution capability of the camera is not necessarily very high.

As well as the seventh embodiment, the CPU 120 determines the part on the "maxillary left buccal side or maxillary right lingual side" based on the outputs of the acceleration sensor 15 (refer to S708 of FIG. 27). Next, the CPU 120 acquires an image from the camera 19 and detects the uvula from the image. A known image analysis technique can be utilized for detecting the uvula. For example, it is thought that the profile of the uvula is detected by edge extraction or Hough transformation or the uvula is detected by pattern matching. When the brush is on the lingual side, the front end of the brush head is directed toward a throat. Thus, there is a high probability that the uvula is found in the image. Meanwhile, when the brush is on the buccal side, the uvula is not found in the image. Therefore, the CPU 120 determines the part on the "maxillary right lingual side" in a case where the uvula can be detected, and determines the part on the "maxillary left buccal side" in a case where the uvula cannot be detected. Similarly, the "maxillary left buccal side" and the "maxillary right lingual side", the "mandibular left lingual side" and the "mandibular right buccal side", and the "mandibular right lingual side" and the "mandibular left buccal side" can be distinguished.

Further, the left and right occlusal surfaces can be also distinguished as the brushing part. The part can be determined to be the occlusal surface or not based on the acceleration component Ax in the x direction, for example. This is because when the occlusal surface is brushed, the brush surface is substantially horizontal, and the output of Ax is almost zero. The part can be also determined to be the occlusal surface or not based on the acceleration component Az in the z direction or the yaw angle γ. The part can be determined to be on the maxilla or the mandible by the upward and downward orientation of the uvula, and determined to be on the left side or the right side by a position of the uvula in the horizontal direction in the image.

As described above, in the present embodiment, the brushing part can be determined more finely than the first embodiment. For example, the upper and lower tooth rows can be divided into 16 parts including the "maxillary anterior buccal side", the "maxillary anterior lingual side", the "maxillary left buccal side", the "maxillary left lingual side", the "maxillary left occlusal surface", the "maxillary right buccal side", the "maxillary right lingual side", the "maxillary right occlusal surface", the "mandibular anterior buccal side", the "mandibular anterior lingual side", the "mandibular left buccal side", the "mandibular left lingual side", the "mandibular left occlusal surface", the "mandibular right buccal side", the "mandibular right lingual side", and the "mandibular right occlusal surface".

In the present embodiment, although the image information is only utilized for distinguishing the buccal side and the lingual side, all the brushing parts are preferably identified by the image information. However, the oral cavity is narrow and an entire positional relationship is not easily understood. Thus, all the brushing parts may be better identified by the image information with the posture information by the acceleration sensor (the acceleration sensor and the gyroscope) rather than only by the image information. In the present embodiment, although the uvula is to be detected, other parts in the oral cavity (such as a tongue, a throat, a tooth, and a gum) may be recognized so as to determine the position and the posture of the brush. For example, when the tongue or the throat is found in the image, the brush can be determined to be on the lingual side.

(Ninth Embodiment)

A configuration in which the posture is detected and the brushing part is identified by a one-axis accelerator sensor is adopted in a ninth embodiment.

A view on the upper side of FIG. 32 shows a state where the tooth surface on the buccal side or the lingual side is being brushed. At this time, the brush angle (the yaw angle γ) is about 90°, the gravitational acceleration component in the x direction is about 1 g or −1 g (positive and negative of the value correspond to the left and right sides of the tooth row), and the gravitational acceleration component in the z direction is substantially zero. Meanwhile, a view on the lower side of FIG. 32 shows a state where the occlusal surface is being brushed. At this time, the brush angle (the yaw angle γ) is substantially zero, the gravitational acceleration component in the x direction is substantially zero, and the gravitational acceleration component in the z direction is about 1 g or −1 g (positive and negative of the value correspond to the left and right sides of the tooth row).

By utilizing such a characteristic, the "tooth surface on the buccal side or lingual side" and the "occlusal surface" can be distinguished only by the x-axis acceleration sensor or the z-axis acceleration sensor, and further the left side and the right side, and the upper side and the lower side can be distinguished.

(Tenth Embodiment)

As described above, the maxillary right buccal side and the maxillary left lingual side are not easily distinguished only by the output signals of the acceleration sensor. This is because a significant difference is not generated in the output signals of the acceleration sensor between the maxillary right buccal side and the maxillary left lingual side. Similarly, the maxillary left buccal side and the maxillary right lingual side, the mandibular right buccal side and the mandibular left lingual side, and the mandibular left buccal side and the mandibular right lingual side are not easily distinguished.

Thus, in a tenth embodiment, a plurality of optical sensors is provided in the brush head, and the brushing part is identified based on output signals of the optical sensors and the output signals of the acceleration sensor. Photodiode sensors, phototransistors and the like can be used as the optical sensors.

Figure 33:
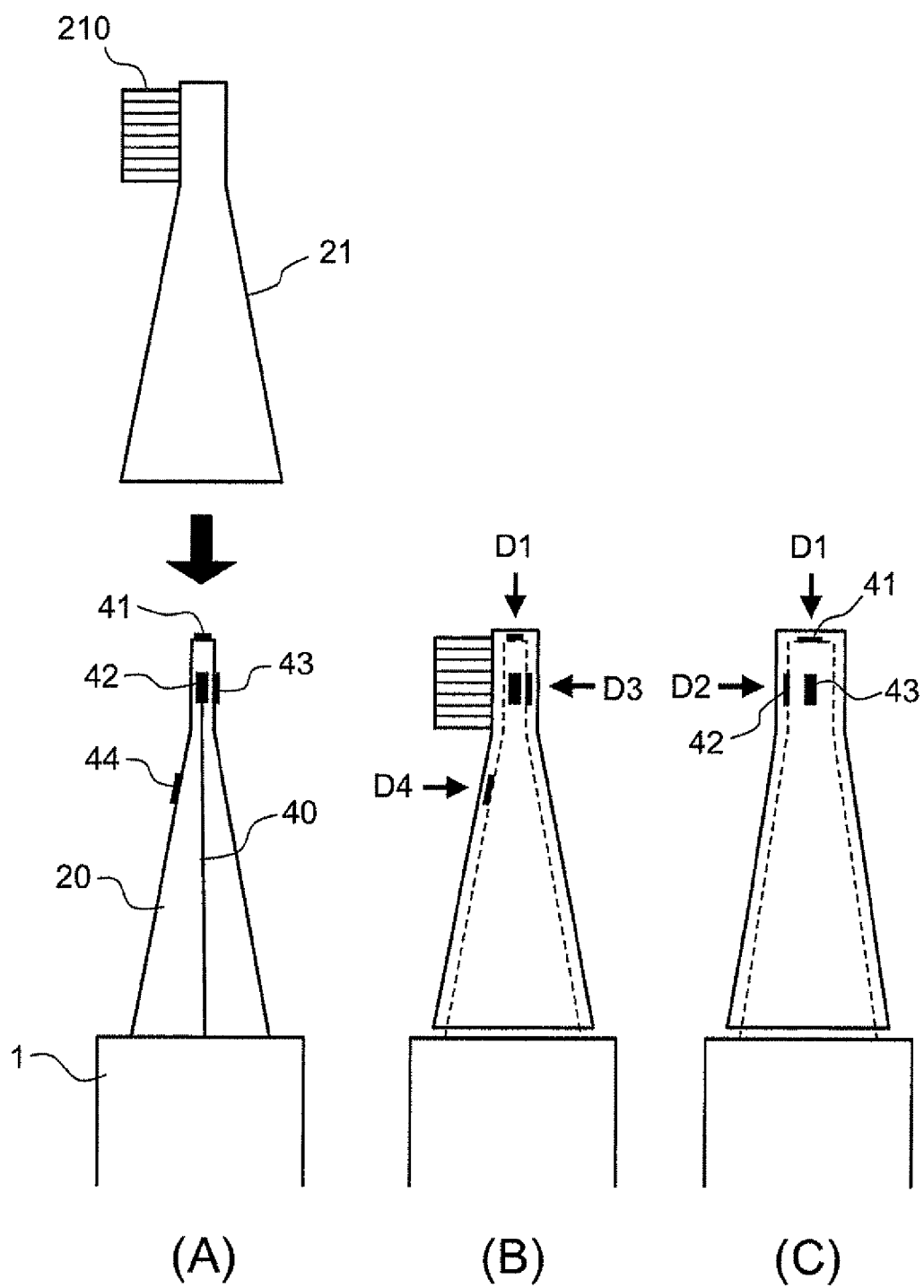
FIGS. 33(A) to 33(C) are views each showing a brush part of an electric toothbrush of a tenth embodiment.

FIGS. 33(A) to (C) show a configuration of an electric toothbrush of the tenth embodiment. FIG. 33(A) shows a state before the brush component 21 is attached to the stem portion 20 of the toothbrush main body 1, and FIG. 33(B) shows a state after the brush component 21 is attached to the stem portion 20. In FIG. 33(C), the view of FIG. 33(B) is seen in the arrow D3 direction (the back surface side of the brush).

As shown in FIG. 33(A), four optical sensors 41, 42, 43, 44 are provided on a surface of the stem portion 20. The optical sensors 41 to 44 are respectively connected to a circuit substrate inside the main body 1 by wires 40, and power supply and signal transmission are performed via the wires 40. Meanwhile, the brush component 21 is made of a highly translucent material. In a state where the brush component 21 is attached to the stem portion 20 as in FIG. 33(B), the optical sensors 41 to 44 can detect light through the brush component 21. The entire brush component 21 is not necessarily made of the highly translucent material but only a part of the optical sensors may be made of the highly translucent material or holes may be provided in the part of the optical sensors. By adopting the configuration in which the optical sensors are provided on the side of the toothbrush main body 1 (the stem portion 20) as described above, a power supply structure of the optical sensors can be simplified. Since the optical sensors are not necessarily provided in the brush component, cost of the brush component serving as the consumable item can be reduced. Although there is a disadvantage in terms of cost, the optical sensors may be provided in the brush component. As a power supply structure in this case, for example, (1) coils may be respectively provided in the brush component 21 and the stem portion 20 so as to supply the power by the electromagnetic induction, or (2) electrodes or connectors may be respectively provided in the brush component 21 and the stem portion 20 so that both are electrically connected when the brush component 21 is attached to the stem portion 20.

As shown in FIGS. 33(B) and (C), the optical sensor 41 is arranged in the front end of the brush head so as to detect light in the arrow D1 direction. The optical sensor 42 is arranged on a side surface of the brush head so as to detect light in the arrow D2 direction. The optical sensor 43 is arranged on a back surface of the brush head so as to detect light in the arrow D3 direction, and the optical sensor 44 is arranged on a front surface of the brush head so as to detect light in the arrow D4 direction. FIG. 34 shows a relationship between the brushing part and the outputs of the optical sensors. In this example, signal strength (brightness) of the outputs of the sensors is evaluated by five stages. For example, when the part on the maxillary left buccal side is being brushed, the optical sensor 43 is closely adhered to the cheek, resulting in a "very dark" state. However, the optical sensor 44 is directed toward the oral cavity, resulting in a "relatively bright" state. Meanwhile, in a case of the maxillary right lingual side which is not easily distinguished from the maxillary left buccal side by the outputs of the acceleration sensor, the optical sensor 43 is directed toward the oral cavity, resulting in the "relatively bright" state, and the optical sensor 44 is directed toward the gum, resulting in a "slightly dark" state. A significant difference is generated between the outputs of the optical sensors in accordance with the brushing part as described above. Thus, by distinguishing by the outputs of a plurality of the optical sensors, the range to which the brushing part belongs can be narrowed down. At this time, the brushing part which is distinguishable by the outputs of the optical sensors is different from the brushing part which is distinguishable by the acceleration sensor. Thus, by supplementing output results of both the sensors to each other, the brushing part can be precisely identified.

Figure 35:
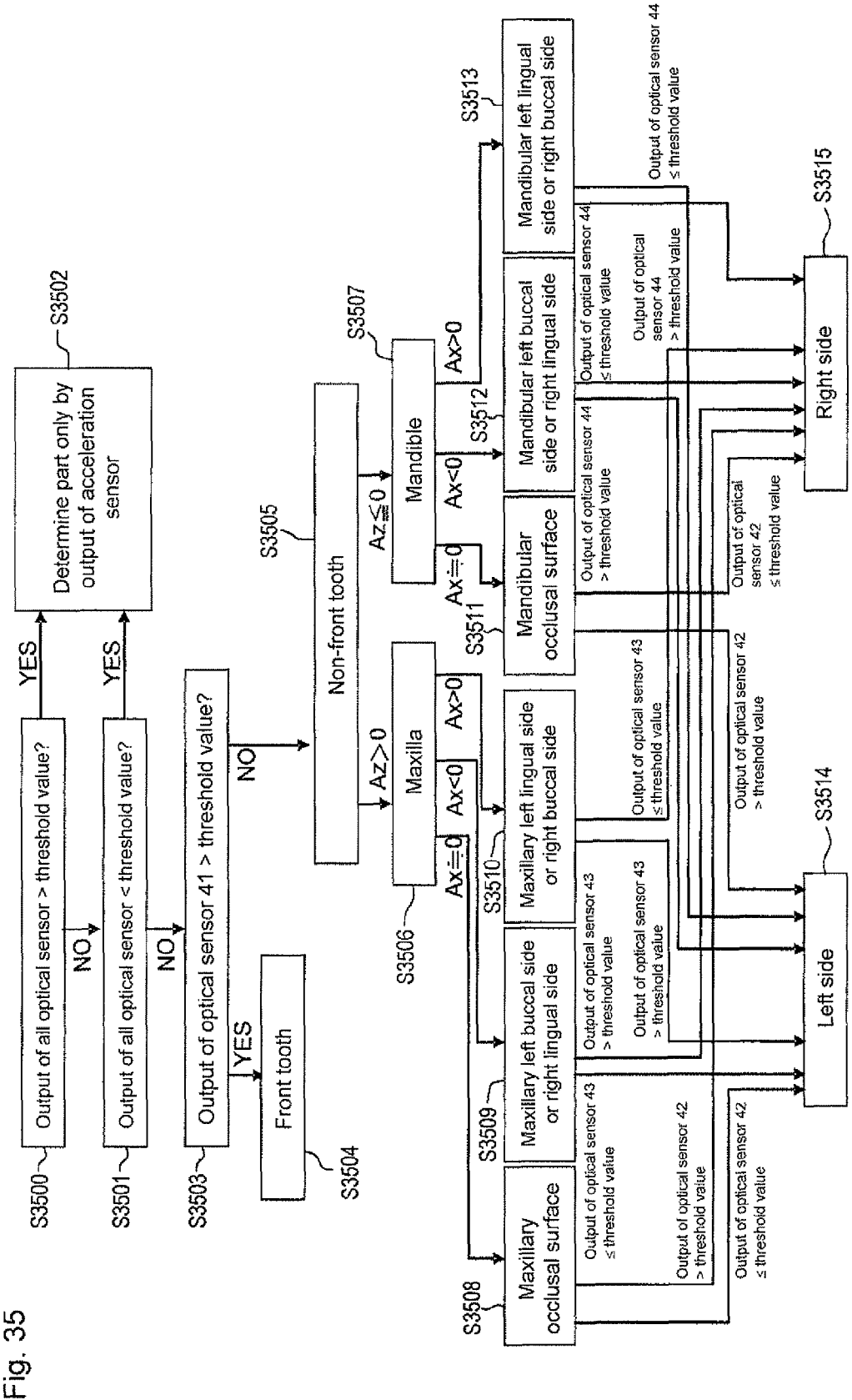
FIG. 35 is a flowchart of a brushing part estimation process of the tenth embodiment.

FIG. 35 is a flowchart showing one example of the brushing part estimation process. A threshold value used for comparison with the outputs of the optical sensors in steps of FIG. 35 is preliminarily fixed by an experiment or the like. The same threshold value may be used in all the steps or a different threshold value may be used for each step.

Upon acquiring the output signals of the optical sensors 41 to 44, the CPU 120 firstly checks whether or not all the outputs of the optical sensors are larger than the threshold value (S3500). In a case where all the outputs of the optical sensors are larger than the threshold value (S3500; YES), there is a possibility that the brush head is placed out of the oral cavity. Since determination cannot be performed by the outputs of the optical sensors in that case, the brushing part is determined only by the outputs of the acceleration sensor (S3502). In the determination process of S3502, for example, the same algorithm as the first embodiment (FIGS. 7 and 8) can be used.

Next, the CPU 120 checks whether or not all the outputs of the optical sensors are smaller than the threshold value (S3501). In a case where all the outputs of the optical sensors are smaller than the threshold value, there is a possibility that a surrounding environment is very dark. In this case, the determination is not easily performed by the outputs of the optical sensors. Thus, again, the brushing part is determined only by the outputs of the acceleration sensor (S3502).

In a case where the determination can be performed by the outputs of the optical sensors (S3501; NO), the CPU 12 firstly checks whether or not the output of the optical sensor 41 is larger than the threshold value (S3503). In a case where the output of the optical sensor 41 is larger (S3503; YES), the part is determined to be the "front tooth" (S3504), and otherwise (S3503; NO), the part is determined to be a "non-front tooth" (S3505). In a case of the "non-front tooth", the CPU 12 determines whether the part is on the "maxilla" (S3506) or the "mandible" (S3507) based on the output Az of the acceleration sensor in the z direction. Next, in a case of the "maxilla", the CPU 12 determines whether the part is on the "occlusal surface" (S3508), the "left buccal side or right lingual side" (S3509), or the "left lingual side or right buccal side" (S3510) based on the output Ax of the acceleration sensor in the x direction. Similarly in a case of the "mandible", the CPU 12 determines whether the part is on the "occlusal surface" (S3511), the "left buccal side or right lingual side" (S3512), or the "left lingual side or right buccal side" (S3513) based on the output Ax of the acceleration sensor in the x direction.

Next, the CPU 12 compares the output of the optical sensor 42, 43 or 44 and the threshold value so as to determine whether the part is on the "left side" (S3514) or the "right side" (S3515). Thereby, the left buccal side and the right lingual side, and the right buccal side and the left lingual side can be distinguished although those are not easily distinguished by the outputs of the acceleration sensor. The processes after the brushing part estimation (such as the brushing time measurement, the brush angle estimation and the brush pressure detection) are the same as the above embodiments.

With the configuration of the present embodiment described above, by combining the outputs of two kinds of sensors, the brushing part can be accurately estimated in detail. Thus, the achievement degree of brushing for each part can be properly evaluated. Therefore, a highly useful and reliable evaluation guideline can be provided to the user.

(Others)

The above configurations of the embodiments only show specific examples of the present invention. The scope of the present invention is not limited to the above embodiments but may be variously modified within the technological scope thereof. For example, the configurations of the above embodiments are preferably combined to each other. In the above embodiments, the vibration type electric toothbrush with the eccentric weight is exemplified. However, the present invention can be applied to other motion type of electric toothbrushes. For example, the present invention can be applied to electric toothbrushes utilizing a rotational reciprocating motion, a linear reciprocating motion, or a brush bristle rotational motion, or switching those in combination. In that case, by switching a motion frequency in accordance with the brushing part or switching between the rotational reciprocating motion and the linear reciprocating motion, the operation mode can be switched. The present invention can be also preferably applied to an electric toothbrush having an ultrasonic vibration element in a brush portion for brushing by vibration of a brush and an ultrasonic wave.

In order to further enhance the precision of the posture detection of the brush and the estimation precision of the brushing part and the brush angle, the movement amount and a relative posture of the brush relative to a reference position are preferably calculated from the outputs of the acceleration sensor and the gyroscope. A posture at the time point when the power supply is turned ON may be set as the reference position, or a mechanism in which the user inputs the reference position (a position where brushing is started) (for example, the user presses the switch in a state where the toothbrush main body is horizontal and the brush is applied to the part on the maxillary anterior buccal side) may be provided. The movement amount (movement distance) can be calculated by double-integrating the respective dynamic acceleration components in the x direction, the y direction and the z direction obtained from the outputs of the acceleration sensor. However, at the time of calculating the movement amount, the coordinate system x, y, z of the toothbrush is converted into the coordinate system X, Y, Z with the direction of the gravitational acceleration as the Z-axis (the above reference position may be the origin). For example, by calculating and accumulating respective movement distances of X, Y, Z for one clock, a relative position to the reference position (an initial position) can be determined. When the relative position to the reference position is determined, the brushing part can be more accurately identified in more detail than the above embodiments. Further, the position of the brush is preferably calculated by utilizing orientation information obtained from a magnetic sensor or the like. The band pass filter such as a high-pass filter can be used for extracting the dynamic acceleration components from the outputs of the acceleration sensor. At this time, in order to eliminate the noise due to the vibration of the brush, the frequency component of about 100 to 300 Hz corresponding to the drive frequency of the brush is preferably cut. The movement amount and the moving direction are preferably more accurately calculated by combining with the gyroscope. Further, with regard to the front tooth, the posture of the brush is changed by 180° according to left and right hands holding the toothbrush main body. Thus, the user registers a dominant hand (a hand holding the toothbrush), and the determination algorithm of the brushing part may be changed or the operation mode (the motor rotation direction, movement of the brush) may be changed in accordance with the registered dominant hand.

In the above embodiments, the three items of the brushing time, the brush angle and the brush pressure are evaluated. However, only one of these may be evaluated. Further, other evaluation items are preferably added.

An uneven shape for guiding (or regulating) a grip position may be provided in the toothbrush main body. For example, when a projection or a recess is provided in a front end part of the toothbrush main body (a position with which finger tips or knuckles of a thumb and a forefinger come into contact when the user grips the toothbrush main body), the user consciously or unconsciously holds the toothbrush so that the fingers match with the projection or the recess. By utilizing this, the user can be guided to a predetermined gripping state. Typically, in a case where the orientation of the brush (the negative direction of the z-axis) is 0° regarding to the angle about the y-axis of FIG. 3, two projections (or recesses) may be provided at positions of about ±45°, and two recesses (or projections) may be provided at positions of about ±135°. When the toothbrush is gripped so that the fingers match with the unevenness, the brush angle is easily maintained at 45°.

In the above embodiments, the CPU 120 of the electric toothbrush 1 executes the processes of the brushing part estimation, the brushing time measurement, the brush angle estimation, the brush pressure detection, the brushing result evaluation and the like. However, part or all of these processes may be executed by an external device which is different from the electric toothbrush main body 1. For example, the outputs of the various sensors provided in the electric toothbrush main body 1 such as the acceleration sensor and the gyroscope are successively forwarded to the external device, and the processes such as the brushing part estimation are executed by a CPU of the external device. By utilizing a resource of the external device having large CPU power for a complicated calculation process and a process including a large volume of calculation, the processes can be executed at high speed. Meanwhile, a low-function CPU can be mounted in the electric toothbrush main body. Thus, cost of the electric toothbrush itself can be reduced and the electric toothbrush can be downsized. Any device in which a CPU is built such as a personal computer and a video game device may be utilized as the external device in addition to the indicator and the charger of the electric toothbrush.

In the above embodiments, the temperature sensor, the camera and the optical sensors are utilized for identifying the brushing part (distinguishing the buccal side and the lingual side). However, in addition, a distance sensor such as an ultrasonic sensor can be also utilized. For example, as well as the temperature sensor of FIG. 26, the distance sensor is installed on the back surface of the brush. In a case where the part on the buccal side is being brushed, the distance sensor comes close to or comes into contact with the cheek. Thus, a measurement value of the distance sensor is a very small value. Meanwhile, in a case where the part on the lingual side is being brushed, the distance sensor is directed toward the oral cavity. Thus, the measurement value of the distance sensor is relatively large. Therefore, by comparing the measurement value of the distance sensor and a threshold value (such as 5 mm), the buccal side and the lingual side can be distinguished.

The invention claimed is:

1. An electric toothbrush, comprising:
   a brush;
   a driver operable to move the brush;
   a posture detection device operable to detect a posture of the brush based on an output of an acceleration sensor;
   a part estimation device operable to estimate a brushing part being brushed among a plurality of parts defined by dividing a surface of a tooth row based on the detected posture;
   a time measurement device operable to measure brushing time for each part;
   an evaluation output device operable to evaluate and output a brushing result for each part based on the measured brushing time;
   a brush angle estimation device operable to estimate a brush angle at each brushing part, said brush angle representing an angle of the brush relative to a tooth axis based on the detected posture; and
   an optimum value or range setting device operable to set optimum values or ranges of brush angles separately for different brushing parts, wherein
   the evaluation output device further evaluates and outputs the brushing result for each brushing part based on a comparison between the estimated brush angle and the optimum value or range set for the corresponding brushing part.

2. The electric toothbrush according to claim 1, further comprising:
   a brush pressure detection device operable to detect brush pressure, wherein
   the evaluation output device further evaluates and outputs the brushing result for each part based on the detected brush pressure.

3. The electric toothbrush according to claim 1, further comprising:
   a brush angle guide device operable to output a guide for informing a user of whether or not the brush angle is proper.

4. The electric toothbrush according to claim 3, wherein the brush angle guide device notifies that the brush angle is at the optimum value or range, or that the brush angle is not at the optimum value or range.

5. The electric toothbrush according to claim 4, wherein the brush angle guide device stepwise changes a notification level in accordance with a degree of a difference between the brush angle and the optimum value or range.

6. The electric toothbrush according to claim 3, wherein the brush angle guide device performs notification with light.

7. The electric toothbrush according to claim 1, further comprising:
   a brushing part guide device operable to determine and guide a part to be brushed next among parts not sufficiently brushed yet based on the brushing result for each part.

8. The electric toothbrush according to claim 7, wherein the brushing part guide device guides a change in the brushing part when a current brushing part is different from the part to be brushed.

9. The electric toothbrush according to claim 1, further comprising:
   a correction circuit operable to eliminate a dynamic acceleration component or a noise from the output of the acceleration sensor.

10. The electric toothbrush according to claim 1, further comprising:
    a correction circuit operable to smooth an output waveform of the acceleration sensor.

11. The electric toothbrush according to claim 1, wherein the driver switches an operation mode of the brush in accordance with the brushing part estimated by the part estimation device.

12. The electric toothbrush according to claim 11, wherein the driver switches a motion frequency of the brush in accordance with the brushing part estimated by the part estimation device.

13. An electric toothbrush, comprising:
    a brush;
    a driver operable to move the brush;
    a posture detection device operable to detect a posture of the brush based on an output of an acceleration sensor;
    a part estimation device operable to estimate a brushing part being brushed among a plurality of parts defined by dividing a surface of a tooth row based on the detected posture;
    a brush angle estimation device operable to estimate a brush angle at each brushing part, said brush angle representing an angle of the brush relative to a tooth axis based on the detected posture;
    an optimum value or range setting device operable to set optimum values or ranges of brush angles separately for different brushing parts; and
    an evaluation output device that evaluates and outputs the brushing result for each brushing part based on a comparison between the estimated brush angle and the optimum value or range set for the corresponding brushing part.

14. The electric toothbrush according to claim 13, further comprising:
    a brush pressure detection device operable to detect brush pressure, wherein the evaluation output device further evaluates and outputs the brushing result for each part based on the detected brush pressure.

15. The electric toothbrush according to claim 13, further comprising:
a brush angle guide device operable to output a guide for informing a user of whether or not the brush angle is proper.

16. The electric toothbrush according to claim 15, wherein the brush angle guide device notifies that the brush angle is at the optimum value or range, or that the brush angle is not at the optimum value or range.

17. The electric toothbrush according to claim 16, wherein the brush angle guide device stepwise changes a notification level in accordance with a degree of a difference between the brush angle and the optimum value or range.

18. The electric toothbrush according to claim 15, wherein the brush angle guide device performs notification with light.

19. The electric toothbrush according to claim 13, further comprising:
a brushing part guide device operable to determine and guide a part to be brushed next among parts not sufficiently brushed yet based on the brushing result for each part.

20. The electric toothbrush according to claim 19, wherein the brushing part guide device guides a change in the brushing part when a current brushing part is different from the part to be brushed.

21. The electric toothbrush according to claim 13, further comprising:
a correction circuit operable to eliminate a dynamic acceleration component or a noise from the output of the acceleration sensor.

22. The electric toothbrush according to claim 13, further comprising:
a correction circuit operable to smooth an output waveform of the acceleration sensor.

23. The electric toothbrush according to claim 13, wherein the driver switches an operation mode of the brush in accordance with the brushing part estimated by the part estimation device.

24. The electric toothbrush according to claim 23, wherein the driver switches a motion frequency of the brush in accordance with the brushing part estimated by the part estimation device.

* * * * *